United States Patent
Curulla-Ferre et al.

(10) Patent No.: US 11,306,049 B2
(45) Date of Patent: *Apr. 19, 2022

(54) PROCESS USING CATALYTIC COMPOSITION FOR THE CONVERSION OF SYNGAS TO HIGHER ALCOHOLS

(71) Applicants: TOTAL SE, Courbevoie (FR); ETH ZURICH, Zurich (CH)

(72) Inventors: Daniel Curulla-Ferre, Uccle (BE); Joseph Stewart, Uccle (BE); Javier Perez-Ramirez, Zürich (CH); Cecilia Mondelli, Zürich (CH); Ho Ting Luk, Zürich (CH)

(73) Assignees: TOTAL SE, Courbevoie (FR); ETH ZURICH, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/424,352

(22) PCT Filed: Jan. 28, 2020

(86) PCT No.: PCT/EP2020/052014
§ 371 (c)(1),
(2) Date: Jul. 20, 2021

(87) PCT Pub. No.: WO2020/157049
PCT Pub. Date: Aug. 6, 2020

(65) Prior Publication Data
US 2022/0089516 A1    Mar. 24, 2022

(30) Foreign Application Priority Data

Feb. 1, 2019 (EP) .................................... 19305122

(51) Int. Cl.
*C07C 29/156* (2006.01)
*C07C 29/153* (2006.01)
(Continued)

(52) U.S. Cl.
CPC ............. *C07C 29/156* (2013.01); *B01J 21/14* (2013.01); *B01J 21/185* (2013.01); *B01J 23/70* (2013.01);
(Continued)

(58) Field of Classification Search
None
See application file for complete search history.

(56) References Cited

U.S. PATENT DOCUMENTS

| | | |
|---|---|---|
| 4,304,871 A | 12/1981 | Brennan et al. |
| 4,595,702 A | 6/1986 | Chu et al. |

(Continued)

FOREIGN PATENT DOCUMENTS

EP    2257366 B1    7/2011

OTHER PUBLICATIONS

Eguchi, K. et al. "High pressure catalytic hydration of olefins over various proton-exchanged zeolites" ChemLett. 1986, vol. 15, No. 4, 567-570 (Year: 1986).*

(Continued)

*Primary Examiner* — Medhanit W Bahta
(74) *Attorney, Agent, or Firm* — Ewing & Jones, PLLC

(57) ABSTRACT

The present disclosure relates to a process for converting syngas to C2+ alcohols, said process comprising the steps of providing a reactor, of providing a catalyst composition and one or more acidic materials within said reactor, of providing a feed stream comprising a mixture of $H_2$ and CO; and of contacting said feed stream with said catalyst composition and said one or more acidic materials under reaction conditions to provide product stream. Said process is remarkable in that said catalyst composition comprises an active phase comprising CuFe deposited on a carbon-containing (Continued)

support, and the one or more acidic materials are one or more zeolites having a Si/Al molar ratio ranging between 2 and 200.

14 Claims, 2 Drawing Sheets

(51) Int. Cl.

| | |
|---|---|
| *C07C 29/151* | (2006.01) |
| *C07C 29/154* | (2006.01) |
| *B01J 23/745* | (2006.01) |
| *B01J 21/18* | (2006.01) |
| *B01J 21/14* | (2006.01) |
| *B01J 23/74* | (2006.01) |
| *B01J 23/70* | (2006.01) |

(52) U.S. Cl.
CPC ............. *B01J 23/74* (2013.01); *B01J 23/745* (2013.01); *C07C 29/151* (2013.01); *C07C 29/153* (2013.01); *C07C 29/154* (2013.01)

(56) References Cited

U.S. PATENT DOCUMENTS

| | | |
|---|---|---|
| 6,703,429 B2 | 3/2004 | O'Rear et al. |
| 7,279,138 B2 | 10/2007 | Pagani et al. |

OTHER PUBLICATIONS

T.-S. Zhao et al., "Selective Synthesis of Middle Isoparaffins via a Two-Stage Fisher-Tropsch Reaction: Activity Investigation for a Hybrid Catalyst", Ind. Eng. Chem. Res., (2005), vol. 44, pp. 769-775.

C. Kibby et al., "Chevron's gas conversion catalysis-hybrid catalysts for wax-free Fisher-Tropsch synthesis", Catal Today, (2013), vol. 215, 11 pages.

G. Yang et al., "Design and modification of zeolite capsule catalyst, a confined reaction field, and its application in one-step isoparaffin synthesis from syngas", Energy & Fuels, (2008), vol. 22, pp. 1463-1468.

X-M. Wu et al., "Co-decorated carbon nanotubes as a promoter of Co—Mo—K oxide catalyst for synthesis of higher alcohols from syngas", Applied Catalysis A, (2008), vol. 340, pp. 87-97.

X. Dong et al., "Preparation and characterization of carbon nanotube-promoted Co—Cu catalyst for higher alcohol synthesis from syngas", Catalysis Today, (2009), vol. 147, pp. 158-165.

Ho Ting Luk et al., "Role of Carbonaceous Supports and Potassium Promoter on Higher Alcohols Synthesis over Copper-Iron Catalysts", ACS Catal., (2018), 56 pages.

Yongwu LU et al., "High Selectivity Higher Alcohols Synthesis from Syngas over Three-Dimensionally Ordered Macroporous Cu—Fe Catalysts"; Chem Cat Chem, (2014), vol. 6, pp. 473-478.

Mingyue Ding et al., "Enhancement of conversion from bio-syngas to higher alcohols fuels over K-promoted Cu—Fe bimodal pore catalysts"; Fuel Process. Technol., (2017), vol. 159, pp. 436-441.

Wa Gao et al., "Catalytic conversion of syngas to mixed alcohols over CuFe-based catalysts derived from layered double hydroxides"; Catal Sci. Technol., (2013), vol. 3, pp. 1324-1332.

Jun Wu et al., "Synergetic catalysis of bimetallic CuCo nanocomposites for selective hydrogenation of bio-derived esters"; ACS Catal., (2017), vol. 7,13 pages.

International Search Report issued in Application No. PCT/EP2020/052014, dated May 20, 2020; 3 pages.

\* cited by examiner

PROCESS USING CATALYTIC COMPOSITION FOR THE CONVERSION OF SYNGAS TO HIGHER ALCOHOLS

CROSS-REFERENCE TO RELATED APPLICATIONS

This application claims the benefit of PCT/EP2020/052014 filed Jan. 28, 2020, which claims priority from EP 19305122.4 filed Feb. 1, 2019, which are incorporated herein by reference in their entireties for all purposes.

FIELD OF THE DISCLOSURE

The present disclosure relates to a process for converting syngas to higher alcohols using catalytic composition.

BACKGROUND OF THE DISCLOSURE

Syngas conversion is well known for producing a variety of chemicals including methanol, alkenes, alkanes. Such products are produced commercially as the methanol synthesis process or the Fischer-Tropsch synthesis (FTS) process. Higher alcohols (C2+) are important compounds with widespread applications in the chemical, pharmaceutical and energy sectors, for instance in the manufacture of pharmaceuticals, detergents, and polymers as well as alternative fuels, gasoline additive and hydrogen carriers. Currently, they are mainly produced by sugar fermentation (ethanol and isobutanol) or hydration of petroleum-derived alkenes. There is currently no commercially process for direct synthesis from syngas. Of the higher alcohols synthesis technologies described in the open literature, alcohol products are predominantly primary alcohols.

Work on this subject was initiated in the 1930s, however, has fluctuated with oil prices. In the last decade, interest has increased significantly in line with the rise of shale gas and renewable resources that can generate gaseous feedstocks. To date, no catalytic system reported has performed sufficiently well to justify an industrial implementation. The majority of systems that have been explored are generally bulk metal catalysts. They are normally split into four main classes: rhodium-based, molybdenum-based, modified Fischer-Tropsch and modified methanol synthesis catalysts. The majority of catalytic systems contain high loadings of their active metals, which limits their economic viability. A variety of metal combinations including CuCo, CuFe and CoMo as either bulk or supported metals have been described. Bulk materials are generally generated via coprecipitation, while supported materials have been prepared through wet-impregnation, sol-gel and incipient wetness, amongst others. A number of Rh-based systems exist but their use is limited due to their high price. Of the supported systems, neutral carriers are widely used.

In the field of the FTS, different efforts have been made in order to find ways to improve the selectivities for desirable products such as upgrading fuel components, including catalyst development and reactor design.

T.-S. Zhao et al., in "*Selective synthesis of middle isoparaffins via a two-stage Fisher-Tropsch Reaction: Activity investigation for a hybrid catalyst*", Ind. Eng. Chem. Res., 2005, 44, 769-775, have successfully synthesised isoalkane hydrocarbons from syngas via FTS in a two-stage reactor using hybrid catalysts with different functions. With $Co/SiO_2$+HZSM-5 in the first-stage reactor at a temperature range of 513 K (239.85° C.) to 523 K (249.85° C.) and H zeolites alone or their hybrid with $Pd/SiO_2$ in the second-stage reactor at a temperature range of 553 K (279.85° C.) to 593 K (319.85° C.), a CO conversion of more than 74% has been obtained. High selectivity of 64.4% has been obtained for the C4-C6 isoalkanes. C1 to C11 hydrocarbons are actually generated after the first-stage reactor. This follows by reactions of hydrocracking and isomerization performed within the second-stage reactor, due to the presence of H zeolites and hydrogen.

U.S. Pat. No. 4,304,871 describes the conversion of syngas to hydrocarbon mixtures utilizing a dual catalyst bed. The first catalyst bed is loaded with iron or cobalt along with a crystalline aluminosilicate. Generation of liquid hydrocarbon products, mainly olefinic products, with a boiling point inferior to 480 K (206.85° C.) was obtained. Those liquid hydrocarbon products are then converted over a second catalyst bed containing HZSM-5 to obtain products rich in aromatics.

C. Kibby et al., in "*Chevron's gas conversion catalysis-hybrid catalysts for wax-free Fisher-Tropsch synthesis*", Catal. Today, 2013, 215, 131-141, have described a hybrid Fisher-Tropsch catalyst being a bimetallic catalyst of CoRu and a zeolite component that reside within a single extruded particle that is sized and shaped for commercial application. Use of this catalyst provides for high yield of C5+ liquid hydrocarbons free of a solid wax phase, with a minimum of C1 to C4 gas products.

G. Yang et al., in "*Design and modification of zeolite capsule catalyst, a confided reaction field, and its application in one-step isoparaffin synthesis from syngas*", Energy & Fuels, 2008, 22, 1463-1468, describe zeolite capsule catalysts utilized for the isoalkane direct synthesis via FTS reaction. These cobalt-based catalysts produce light isoalkanes as well as olefinic compounds. When combined to a second catalytic bed composed of $Pd/SiO_2$, almost all the olefinic compounds are hydrogenated and converted to isoalkanes.

U.S. Pat. No. 4,595,702 describes the conversion of syngas into liquid hydrocarbons in the C5 to C24 boiling range of gasoline and diesel fuel with a physical mixture of an iron-based catalyst and zeolite, wherein the nitrogen content is low. The formation of higher alcohols by this process is not referred to.

U.S. Pat. No. 6,703,429 describes a process for converting syngas into hydrocarbons. A first process, a dual functional syngas conversion, for the conversion of syngas to higher molecular weight products is carried out and uses two different types of catalysts and involves making a methanol intermediate over one catalyst followed by rapid consumption of that intermediate over a second catalyst while the reaction mixture remains in the same reactor. The catalyst for making methanol includes iron and may also include transition metals such as copper. The catalyst for converting methanol to aromatics and isoalkanes typically includes one or more zeolites. Depending on the acidic nature of the one or more zeolites, aromatics (when the zeolites tend to be relatively acidic) or isoalkanes (when the zeolite tend to be relatively non-acidic) are generated. A further process is used to convert unreacted syngas to linear alkanes and linear alkenes, along with linear C3-C4 alcohols. The linear alkenes are finally alkylated with the isoalkanes produced in the dual functional syngas conversion to produce high octane gasoline range alkylate.

As can be seen from the prior art, many of the catalyst tests reported so far have been optimized to give a high yield of light (iso)alkanes. With regard to the improvement of the selectivities of higher alcohols, the effort has been rather concentrated, among others, in the development of suitable carriers for the catalyst.

X-M. Wu et al., in "*Co-decorated carbon nanotubes as a promoter of Co—Mo—K oxide catalyst for synthesis of higher alcohols from syngas*", Applied Catalysis A, 340 (2008) 87-97, have reported a metal cobalt-decorated multi-walled carbon nanotube promoted Co—Mo—K oxide-based catalyst. Under reaction conditions of 5.0 MPa and 593 K (319.85° C.), the space-time yield of C2-C9 alcohols reached 0.628 $g_{HA}g_{cat}^{-1}$ $h^{-1}$. However, a selectivity into $CO_2$ of more than 20% has been reported and methanol has been generated in quantities superior or equal to 9%.

X. Dong et al., in "*Preparation and characterization of carbon nanotube-promoted Co-Cu catalyst for higher alcohol synthesis from syngas*", Catalysis Today, 147 (2009), 158-165, have described a cobalt-copper promoted by "her-ringbone-type" multiwalled carbon nanotubes. Under reaction conditions of 5.0 MPa and 573 K (299.85° C.), the space-time yield of C2-C8 alcohols reached 0.611 $g_{HA}g_{cat}^{-1}$ $h^{-1}$. However, a selectivity into $CO_2$ of 5% has been reported, more than 11% of the CO has been converted into dimethyl ether and methanol was also generated.

Ho Ting Luk et al., in ACS Catal. 2018, 8, 9604-9618 described the role of carbonaceous supports and potassium promoter on higher alcohols synthesis over copper-iron catalysts.

Yongwu Lu et al., in Chem Cat Chem 2014, 6, 473-478 described the production of higher alcohols from syngas over three-dimensionally ordered macroporous Cu—Fe catalysts. The selectivity obtained toward higher alcohols was considered high by the authors.

There is still a need for a catalyst and a process of HAS with high selectivity to high alcohols and limited methanol, dimethyl ether (DME), and carbon dioxide production.

SUMMARY OF THE DISCLOSURE

It is an object of the disclosure to provide a new process for HAS from syngas. Another object is to provide a new process for HAS from syngas allowing improvement in CO conversion to higher alcohols. A further object is to provide a new process for HAS from syngas allowing improvement in CO conversion together with limited $CO_2$ production. A yet another object is to provide a new process for HAS from syngas allowing improvement in productivity of secondary higher alcohols. The present disclosure provides a solution to one or more of the aforementioned needs.

According to a first aspect, the disclosure provides a process for converting syngas to C2+ alcohols, said process comprising the following steps:
a) providing an installation comprising at least one reactor having one or more catalytic beds;
b) providing a catalyst composition and one or more acidic materials within said at least one reactor;
c) providing a feed stream comprising a mixture of $H_2$ and CO;
d) contacting said feed stream with said catalyst composition and said one or more acidic materials under reaction conditions to provide product stream;
said process is remarkable in that said catalyst composition comprises an active phase comprising CuFe deposited on a carbon-containing support, the total content of iron and copper ranging from 1 to 10 wt. % based on the total weight of the catalyst composition and as determined by inductively coupled plasma optical emission spectroscopy, and the one or more acidic materials being one or more zeolites having a Si/Al molar ratio ranging between 2 and 200 as determined by inductively coupled plasma-optical emission spectroscopy.

Surprisingly, it has been found that high yield in the conversion of C2+ alcohols can be achieved by using the process of the present disclosure. A selectivity in C2+ alcohols of at least 30% at a CO conversion rate of 4% has been attained while no more than 3% of methanol is generated at this rate of conversion. Those results provide a distribution of products more favourable than when the acid materials are absent since in some cases, no methanol at all is generated. Additionally, it has been noted that the present disclosure provides for a process wherein the generation of $CO_2$ (at most 20%), of methanol (at most 7%) and of DME (at most 7%) that are limited.

The Catalyst Composition

The catalyst composition comprises an active phase comprising CuFe deposited on a carbon-containing support, the total content of iron and copper ranging from 1 to 10 wt. % based on the total weight of the catalyst composition and as determined by inductively coupled plasma optical emission spectroscopy.

With preference, one or more of the following examples can be used to better define the carbon-containing support of the catalyst composition of the present disclosure:
  The carbon-containing support is selected from carbon nanofibers and/or carbon nanotubes; for example, the carbon-containing support of the catalyst composition is or comprises carbon nanofibers; for example, the carbon-containing support of the catalyst composition comprises at least 80 wt. % of carbon nanofibers based on the total weight of the carbon-containing support.
  The carbon-containing support is selected from carbon nanofibers and/or carbon nanotubes; and has a hollow-core structure with an inner diameter of at least 17 nm as determined according to $N_2$ sorption analysis, preferentially of at least 20 nm, more preferentially of at least 25 nm, even more preferentially of at least 30 nm.
  The carbon-containing support is or comprises carbon nanofibers selected from platelet-type carbon nanofibers and conical platelet-type carbon nanofibers; with preference, the carbon-containing support is or comprises conical platelet-type carbon nanofibers.
  The carbon-containing support is conical platelet-type carbon nanofibers being iron-free, i.e. conical platelet-type carbon nanofibers having a content of iron less than 100 ppm based on the total weight of the conical platelet-type carbon nanofibers.

With preference, one or more of the following examples can be used to further define the catalyst composition of the present disclosure:
  The catalyst composition further comprises at least one promoter.
  The catalyst composition further comprises at least one promoter selected from alkali and alkaline earth metals, preferably at least one promoter selected from an alkali metal, more preferably at least one promoter is potassium.
  The catalyst composition further comprises at least one promoter and the content of at least one promoter is ranging from 0.001 to 0.5 wt. % based on the total weight of the catalyst composition and as determined by inductively coupled plasma optical emission spectroscopy, preferably from 0.001 to 0.4 wt. %, more preferably from 0.001 to 0.3 wt. %, even more preferably from 0.001 to 0.2 wt. %, most preferably from 0.001 to 0.1 wt. %, even most preferably from 0.002 to 0.05 wt. %, or preferably from 0.003 to 0.03 wt. %, or more preferably from 0.004 to 0.02 wt. % or more preferably from 0.005 to 0.01 wt. % or more preferably from 0.006 to 0.009 wt. %.

The Cu/Fe bulk molar ratio is ranging from 0.5/1 to 5/1, preferably from 1/1 to 4/1, more preferably from 1.2/1 to 3/1; even more preferably from 1.5/1 to 2.5/1; most preferably the Cu/Fe bulk molar ratio is 2/1.

The Cu particle size is at least 7 nm as determined from the (111) reflection in an XRD pattern using the Scherrer equation, preferably at least 8 nm, more preferably at least 9 nm.

The Cu particle size is at most 35 nm as determined from the (111) reflection in an XRD pattern using the Scherrer equation, preferably at most 30 nm, more preferably at most 25 nm, even more preferably at most 20 nm, most preferably at most 15 nm, and even most preferably at most 11 nm.

The Cu particle size is ranging from 7 to 35 nm as determined from the (111) reflection in an XRD pattern using the Scherrer equation, preferably from 7 to 30 nm, more preferably from 7 to 25 nm, even more preferably from 7 to 20 nm, most preferably from 8 to 15 nm, and even most preferably ranging from 9 to 11 nm.

The total content of iron and copper is ranging from 2.0 to 8.0 wt. % based on the total weight of the catalyst composition as determined by inductively coupled plasma optical emission spectroscopy, preferably ranging from 3.0 to 7.0 wt. %, more preferably from 4.0 to 6.0 wt. %; even more preferably from 4.5 to 5.5 wt. % and most preferably below 5.0 wt. %.

The catalyst composition is a reduced catalyst composition.

The catalyst composition is reduced over hydrogen gas before step (c).

The catalyst composition is a reduced catalyst composition as determined by X-ray diffraction wherein the reduced catalyst is devoid of iron oxide.

The catalyst composition is a reduced composition having a Brunauer-Emmett-Teller (BET) surface area in the range of 20 m$^2$ g$^{-1}$ to 300 m$^2$ g$^{-1}$ as determined according to N$_2$ sorption analysis, preferably in the range of 20 m$^2$ g$^{-1}$ to 200 m$^2$ g$^{-1}$.

For example, the catalyst composition is remarkable in that the support is a carbon-containing support selected from carbon nanofibers and/or carbon nanotubes, in that the total content of iron and copper is ranging from 1 to 10 wt. % based on the total weight of the catalyst composition and as determined by inductively coupled plasma optical emission spectroscopy, and in that the Cu/Fe bulk molar ratio is ranging from 0.5/1 to 5/1.

For example, the catalyst composition is remarkable in that the support is a carbon-containing support selected from carbon nanofibers and/or carbon nanotubes, in that the total content of iron and copper is ranging from 1 to 10 wt. % based on the total weight of the catalyst composition and as determined by inductively coupled plasma optical emission spectroscopy, in that the Cu/Fe bulk molar ratio is ranging from 0.5/1 to 5/1, and in that the composition further comprises at least one promoter selected from alkali and alkaline earth metals; with preference the at least one promoter is potassium.

For example, the catalyst composition is remarkable in that the support is a carbon-containing support selected from carbon nanofibers and/or carbon nanotubes, in that the total content of iron and copper is ranging from 1 to 10 wt. % based on the total weight of the catalyst composition and as determined by inductively coupled plasma optical emission spectroscopy, in that the Cu/Fe bulk molar ratio is ranging from 0.5/1 to 5/1, in that the composition further comprises at least one promoter selected from alkali and alkaline earth metals, and in that the carbon-containing support has hollow-core structure with an inner diameter of at least 17 nm as determined according to N$_2$ sorption analysis.

The One or More Acidic Materials

The one or more acidic materials are one or more zeolites having a Si/Al molar ratio ranging between 2 and 200 as determined by inductively coupled plasma-optical emission spectroscopy.

With preference, one or more of the following examples can be used to better define the one or more acidic materials of the present disclosure:

- The one or more acidic materials are one or more zeolites are selected from MFI, FAU, MOR, FER, BEA, TON, MTT, OFF families, or any mixture thereof. With preference, the one or more zeolites are selected from the MFI family and/or MOR family. With preference, the one or more zeolites are selected from the MFI family. More preferably, the one or more zeolites are or comprise ZSM-5.
- The one or more zeolites comprise at least one 10-membered ring channel and/or at least one 12-membered ring channel.
- The one or more zeolites are partially ion-exchanged with an alkali metal-based ion, preferably with potassium.
- The one or more zeolites have a surface area comprised between 10 m$^2$ g$^{-1}$ and 1000 m$^2$ g$^{-1}$ as determined by the Brunauer-Emmett-Teller (BET) method, preferably comprised between 250 m$^2$ g$^{-1}$ and 900 m$^2$ g$^{-1}$, more preferably comprised between 300 m$^2$ g$^{-1}$ and 800 m$^2$ g$^{-1}$.
- The one or more zeolites have pore volume comprised between 0.15 cm$^3$ g$^{-1}$ and 1.25 cm$^3$ g$^{-1}$, as determined by N$_2$ sorption analysis, preferably between 0.18 cm$^3$ g$^{-1}$ and 1.00 cm$^3$ g$^{-1}$, more preferably between 0.16 cm$^3$ g$^{-1}$ and 0.70 cm$^3$ g$^{-1}$, even more preferably between 0.20 cm$^3$ g$^{-1}$ and 0.60 cm$^3$ g$^{-1}$.
- The one or more zeolites have a density of Brønsted-acid sites ranging from 5 µmol g$^{-1}$ to 700 µmol g$^{-1}$ as determined by Fourier transform infrared spectroscopy of adsorbed pyridine, preferably from 40 µmol g$^{-1}$ to 600 µmol g$^{-1}$, more preferably from 50 µmol g$^{-1}$ to 500 µmol g$^{-1}$.
- The one or more zeolites have a density of Brønsted-acid sites of less than 200 µmol g$^{-1}$ as determined by Fourier transform infrared spectroscopy of adsorbed pyridine, preferably of less than 150 µmol g$^{-1}$, more preferably of less than 100 µmol g$^{-1}$; and/or of at least 5 µmol g$^{-1}$, preferentially of at least 25 µmol g$^{-1}$, more preferentially of at least 40 µmol g$^{-1}$.
- The one or more zeolites have a density of Lewis-acid sites ranging from 4 µmol g$^{-1}$ to 250 µmol g$^{-1}$ as determined by Fourier transform infrared spectroscopy of adsorbed pyridine, preferably from 15 µmol g$^{-1}$ to 150 µmol g$^{-1}$.
- The one or more zeolites have a density of Lewis-acid sites of less than 50 µmol g$^{-1}$ as determined by Fourier transform infrared spectroscopy of adsorbed pyridine, preferably of less than 40 µmol g$^{-1}$; more preferably of less than 15 µmol g$^{-1}$; and/or of at least 4 µmol g$^{-1}$, preferentially of at least 8 µmol g$^{-1}$.
- The one or more zeolites have a crystal size comprised between 20 nm and 10 µm as determined by Scanning Electron Microscopy (SEM), preferably between 50 nm and 8 µm, more preferably between 70 nm and 5 µm, and most preferably between 100 nm and 2 µm.

For example, the one or more zeolites have a Si/Al molar ratio ranging from 10 to 190 as determined by inductively coupled plasma optical emission spectroscopy, preferably from 12 and 160, more preferably from 15 to 140.

In an example, the one or more zeolites have a Si/Al molar ratio ranging between 2 and 100 as determined by inductively coupled plasma-optical emission spectroscopy, preferably between 5 and 90, more preferably between 10 and 70, even more preferably between 30 and 60, most preferably between 40 and 50.

In another example, the one or more zeolites have a Si/Al molar ratio ranging 100 and 200 as determined by inductively coupled plasma-optical emission spectroscopy, preferably between 110 and 190, more preferably between 120 and 180, even more preferably between 130 and 160.

For example, the one or more acidic materials are one or more MFI zeolites having a Si/Al molar ratio ranging between 2 and 200 as determined by inductively coupled plasma-optical emission spectroscopy, said one or more MFI zeolites being partially ion-exchanged with an alkali-metal based ion.

For example, the one or more acidic materials are one or more MFI zeolites having a Si/Al molar ratio ranging between 2 and 200 as determined by inductively coupled plasma-optical emission spectroscopy, said one or more MFI zeolites are ZMS-5.

For example, the one or more acidic materials are one or more MFI zeolites having a Si/Al molar ratio ranging between 2 and 200 as determined by inductively coupled plasma-optical emission spectroscopy, said one or more MFI zeolites are one or more ZMS-5 zeolites being partially ion-exchanged with an alkali-metal based ion.

For example, the one or more acidic materials are one or more MOR zeolites having a Si/Al molar ratio ranging between 2 and 200 as determined by inductively coupled plasma-optical emission spectroscopy, said one or more MOR zeolites being partially ion-exchanged with an alkali-metal based ion.

For example, the one or more acidic materials are one or more MOR zeolites having a Si/Al molar ratio ranging between 2 and 200 as determined by inductively coupled plasma-optical emission spectroscopy, said one or more MOR zeolites are mordenite.

For example, the one or more acidic materials are one or more MOR zeolites having a Si/Al molar ratio ranging between 2 and 200 as determined by inductively coupled plasma-optical emission spectroscopy, said one or more MOR zeolites are one or more mordenite zeolites being partially ion-exchanged with an alkali-metal based ion.

For example, the one or more acidic materials are one or more BEA zeolites having a Si/Al molar ratio ranging between 2 and 200 as determined by inductively coupled plasma-optical emission spectroscopy, said one or more BEA zeolites being partially ion-exchanged with an alkali-metal based ion.

For example, the one or more acidic materials are one or more BEA zeolites having a Si/Al molar ratio ranging between 2 and 200 as determined by inductively coupled plasma-optical emission spectroscopy, said one or more BEA zeolites are beta zeolites.

For example, the one or more acidic materials are one or more BEA zeolites having a Si/Al molar ratio ranging between 2 and 200 as determined by inductively coupled plasma-optical emission spectroscopy, said one or more BEA zeolites are one or more beta zeolites being partially ion-exchanged with an alkali-metal based ion.

The examples concerning the catalyst composition and the examples concerning the one or more acidic materials can be combined with each other.

For example, the weight ratio of the catalyst composition and the one or more acidic materials is ranging between 0.1 and 10, preferably between 0.2 and 5, more preferably between 0.3 and 3, most preferably between 0.5 and 2.

The Process Conditions

No matter the combination chosen for the catalyst composition and the one or more acidic materials, one or more of the following embodiments and examples can be used to better define the process of the disclosure.

In a first preferred embodiment, wherein said at least one reactor comprises a first reactive bed and one or more subsequent reactive beds, one or more subsequent reactive beds being arranged downstream of the first reactive bed, the process is remarkable in that the catalyst composition and the one or more acidic materials are provided in different reactive beds, and in that the catalyst composition is provided in the first reactive bed and the one or more acidic materials are provided in the one or more subsequent reactive beds.

In a second embodiment, wherein said at least one reactor comprises a first reactive bed and optional one or more subsequent reactive beds, wherein the one or more subsequent reactive beds, when present, are arranged downstream of the first reactive bed, the process is remarkable in that during step (b) a mixture of the catalyst composition and of the one or more acidic materials is provided in the first reactive bed; with preference, one or more acidic materials are provided in the one or more subsequent reactive beds. In said embodiment, the first reactive bed is a mixed bed.

Whatever is the embodiment selected, the one or more of the following features can be used to further define the reaction conditions in the first reactive bed:

The reaction conditions comprise a reaction temperature ranging from 443 K (169.85° C.) to 653 K (379.85° C.), preferably from 493 K (219.85° C.) to 553 (279.85° C.), more preferably from 513 K (239.85° C.) to 548 K (274.85° C.), and even more preferably at a reaction temperature of 543 K (269.85° C.).

The reaction conditions comprise a reaction pressure range ranging from 1 MPa to 10 MPa, preferably from 2 to 9 MPa, preferably from 3 to 7 MPa, more preferably from 4 to 6 MPa, and even more preferably at a reaction pressure of 5 MPa.

The reaction conditions comprise a weight hourly space velocity ranging from 500 cm$^3$ g$_{cat}^{-1}$ h$^{-1}$ to 48,000 cm$^3$ g$_{ca}^{-1}$ h$^{-1}$, preferably from 6,000 cm$^3$ g$_{cat}^{-1}$ h$^{-1}$ to 34,000 cm$^3$ g$_{cat}^{-1}$ h$^{-1}$, more preferably from 8,000 cm$^3$ g$_{cat}^{-1}$ h$^{-1}$ to 32,000 cm$^3$ g$_{cat}^{-1}$ h$^{-1}$; even more preferably from 14,000 cm$^3$ g$_{cat}^{-1}$ h$^{-1}$ to 28,000 cm$^3$ g$_{cat}^{-1}$ h$^{-1}$, most preferably from 16,000 cm$^3$ g$_{cat}^{-1}$ h$^{-1}$ to 24,000 cm$^3$ g$_{cat}^{-1}$ h$^{-1}$.

The reaction conditions comprise a weight hourly space velocity of at least 500 cm$^3$ g$_{cat}^{-1}$ h$^{-1}$, preferably at least 1,000 cm$^3$ g$_{cat}^{-1}$ h$^{-1}$, more preferably of at least 2,000 cm$^3$ g$_{cat}^{-1}$ h$^{-1}$, even more preferably at least 4,000 cm$^3$ g$_{cat}^{-1}$ h$^{-1}$, most preferably at least 6,000 cm$^3$ g$_{cat}^{-1}$ h$^{-1}$, and even most preferably at least 8,000 cm$^3$ g$_{cat}^{-1}$ h$^{-1}$.

The reaction conditions comprise a weight hourly space velocity of at most 48,000 cm$^3$ g$_{cat}^{-1}$ h$^{-1}$, preferably at most 34,000 cm$^3$ g$_{cat}^{-1}$ h$^{-1}$, more preferably of at most 32,000 cm$^3$ g$_{cat}^{-1}$ h$^{-1}$.

With preference; the process is carried out in a reactor comprising two reactive beds, preferably in a dual-bed reactor. In an example, the first and one or more subsequent reactive beds are spatially separated, preferentially by a layer of quartz wool, or by an inert diluent or by any suitable spacer.

Whatever is the example selected, the one or more of the following features can be used to further define the reaction conditions in the one or more subsequent reactive beds.

The reaction conditions comprise a reaction temperature ranging from 373 K (99.85° C.) to 773 K (499.85° C.), preferably from 393 K (119.85° C.) to 673 K (399.85° C.).

The reaction conditions comprise a reaction temperature of at least 373 K (99.95° C.), preferentially of at least 398 K (124.85° C.), more preferentially of at least 403 K (129.85° C.), even more preferably of at least 418 K (139.85° C.) and most preferably of at least 423 K (149.85° C.).

The reaction conditions comprise a reaction temperature of at most 773 K (499.85° C.), preferentially of at most 573 K (299.85° C.).

The reaction conditions of the one or more subsequent reactive beds comprise a reaction temperature that can be the same or different as in the first reactive bed.

The reaction conditions comprise a reaction pressure ranging from 0.1 MPa to 10.0 MPa, preferably ranging from 0.5 MPa to 8.0 MPa, more preferably ranging from 1.0 MPa to 7.0 MPa.

The reaction conditions comprise a reaction pressure of at least 1.0 MPa, preferentially of at least 1.5 MPa, more preferably of at least 2.0 MPa.

The reaction conditions comprise a reaction pressure of at most 10.0 MPa, preferably of at most 6.5 MPa, more preferably of at most 6.0 MPa.

The reaction conditions of the one or more subsequent reactive beds comprise a reaction pressure that can be the same or different as in the first reactive beds.

The reaction conditions comprise a weight hourly space velocity ranging from 500 cm$^3$ g$_{cat}^{-1}$ h$^{-1}$ to 50,000 cm$^3$ g$_{cat}^{-1}$ h$^{-1}$, preferably from 2,000 cm$^3$ g$_{cat}^{-1}$ h$^{-1}$ to 40,000 cm$^3$ g$_{cat}^{-1}$ h$^{-1}$, more preferably from 4,000 cm$^3$ g$_{cat}^{-1}$ h$^{-1}$ to 35,000 cm$^3$ g$_{cat}^{-1}$ h$^{-1}$, even more preferably from 6,000 cm$^3$ g$_{cat}^{-1}$ h$^{-1}$ to 32,000 cm$^3$ g$_{cat}^{-1}$ h$^{-1}$.

The reaction conditions comprise a weight hourly space velocity of at least 2,000 cm$^3$ g$_{cat}^{-1}$ h$^{-1}$, preferably at least 4,000 cm$^3$ g$_{cat}^{-1}$ h$^{-1}$, more preferably of at least 6,000 cm$^3$ g$_{cat}^{-1}$ h$^{-1}$, even more preferably at least 8,000 cm$^3$ g$_{cat}^{-1}$ h$^{-1}$.

The reaction conditions comprise a weight hourly space velocity of at most 50,000 cm$^3$ g$_{cat}^{-1}$ h$^{-1}$, preferably at most 40,000 cm$^3$ g$_{cat}^{-1}$ h$^{-1}$, more preferably at most 35,000 cm$^3$ g$_{cat}^{-1}$ h$^{-1}$, even more preferably at most 32,000 cm$^3$ g$_{cat}^{-1}$ h$^{-1}$.

The process is carried out in a gaseous phase.

The process is carried out in a continuous-flow reactor.

The Syngas Feed Stream

With preference, one or more of the following examples can be used to better define the syngas feed stream used in the process of the present disclosure:

The syngas feed stream has a molar H$_2$/carbon oxides ratio ranging from 0.5/1 to 12.0/1, preferably ranging from 0.5/1 to 10.0/1, more preferably ranging from 0.5/1 to 8.0/1, even more preferably ranging from 0.5/1 to 6.0/1, most preferably ranging from 0.5/1 to 4.0/1, even most preferably ranging from 0.7/1 to 3.0/1, or preferably ranging from 1.0/1 to 2.5/1, or more preferably ranging from 1.2/1 to 2.2/1, or most preferably is 2.0/1; wherein the carbon oxide comprises CO and/or CO$_2$, preferably a mixture of CO and C02.

The syngas feed stream has a molar H$_2$/CO ratio ranging from 0.5/1 to 12.0/1, preferably ranging from 0.5/1 to 10.0/1, more preferably ranging from 0.5/1 to 8.0/1, even more preferably ranging from 0.5/1 to 6.0/1, most preferably ranging from 0.5/1 to 4.0/1, even most preferably ranging from 0.7/1 to 3.0/1, or preferably ranging from 1.0/1 to 2.5/1, or more preferably ranging from 1.2/1 to 2.2/1.

The syngas feed stream comprises at least 5 mol % of CO based on the total molar content of the syngas feed, preferably at least 15 mol %, more preferably at least 17 mol %, more preferably at least 20 mol %.

The syngas feed stream comprises at least 20 mol % of H$_2$ based on the total molar content of the syngas feed, preferably at least 25 mol %, more preferably at least 27 mol %, more preferably at least 30 mol %.

The syngas feed stream comprises a mixture of carbon monoxide (CO) and of carbon dioxide (CO$_2$); or the syngas feed stream is devoid of carbon dioxide (CO$_2$).

The syngas feed stream comprises a mixture of carbon monoxide (CO) and of carbon dioxide (CO$_2$) with the content of CO$_2$ being at most 10 mol % based on the total molar content of the syngas feed, preferably ranging from 0.1 to 10 mol %, more preferably ranging from 0.5 to 8.0 mol %, even more preferably ranging from 1.0 to 6.0 mol %, and most preferably ranging from 3.0 to 5.0 mol %.

The process is carried out during more than 100 hours without replacement or reactivation of the catalyst composition, preferably more than 500 hours.

The process further comprises a step (e) of recovering the product stream containing higher alcohols.

According to a second aspect, the disclosure provides a mixture comprising a catalyst composition and the one or more acidic materials, for use in a process according to the second example of the process according to the first aspect wherein said catalyst composition comprises an active phase comprising CuFe deposited on a carbon-containing support, the total content of iron and copper ranging from 1 to 10 wt. % based on the total weight of the catalyst composition and as determined by inductively coupled plasma optical emission spectroscopy, and the one or more acidic materials being one or more zeolites having a Si/Al molar ratio ranging between 2 and 200 as determined by inductively coupled plasma-optical emission spectroscopy.

DETAILED DESCRIPTION

Figure 1:
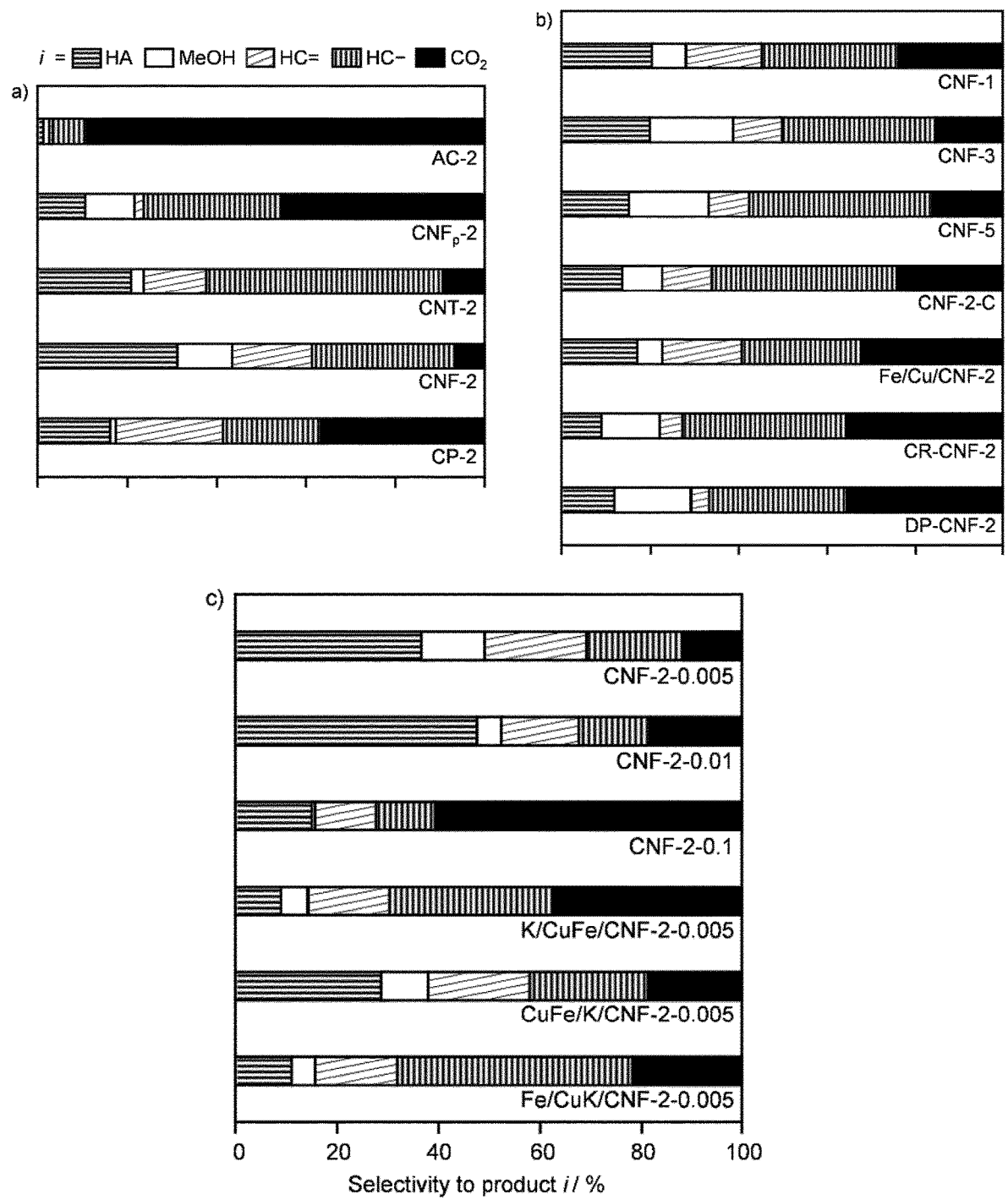
FIG. 1 illustrates the selectivity to product i at a CO conversion level of 7-8% over a) Cu—Fe catalysts in bulk form and supported on different carbonaceous materials, b) Cu—Fe catalysts supported on CNF with variable Cu/Fe molar ratio and prepared by different synthesis methods, and c) Cu—Fe catalysts supported on CNF and promoted with K. Reaction conditions: 543 K, 5 MPa, and molar H$_2$/CO=2.

For the purpose of the disclosure, the following definitions are given:

As used herein, the terms "catalyst composition" refer to a composition comprising a main active phase on a support, and an optional alkali promoter. The term catalyst may refer to both a "bulk catalyst" and a "supported catalyst". A bulk catalyst is a catalyst comprising copper and iron. A supported catalyst comprises or consists of the bulk catalyst (i.e. the Cu—Fe catalyst and optional promoter) and a support. The metals Cu—Fe are the main active phase, i.e. the active phase, of the supported catalyst.

The terms "alkane" or "alkanes" as used herein describe acyclic branched or unbranched hydrocarbons having the general formula $C_nH_{2n+2}$, and therefore consisting entirely of hydrogen atoms and saturated carbon atoms; see e.g. IUPAC. Compendium of Chemical Terminology, 2nd ed. (1997). The term "alkanes" accordingly describes unbranched alkanes ("normal-paraffins" or "n-paraffins" or "n-alkanes" or "paraffins") and branched alkanes ("iso-paraffins" or "iso-alkanes") but excludes naphthenes (cycloalkanes). They are sometimes referred to by the symbol "HC—".

The terms "olefin" or "alkene" as used herein relate to an unsaturated hydrocarbon compound containing at least one carbon-carbon double bond. They are sometimes referred to by the symbol "HC=". The term "alkene" accordingly describes branched alkenes and unbranched alkenes. The term "alkene" accordingly also describes linear alkenes.

The term "hydrocarbon" refers to the alkanes (saturated hydrocarbons) and the alkenes (unsaturated hydrocarbons) together.

As used herein, the terms "C # alcohols", "C # alkenes", or "C # hydrocarbons", wherein "#" is a positive integer, is meant to describe respectively all alcohols, alkenes, or hydrocarbons having # carbon atoms. Moreover, the term "C #+ alcohols", "C #+ alkenes", or "C #+ hydrocarbons", is meant to describe all alcohol molecules, alkenes molecules or hydrocarbons molecules having # or more carbon atoms. Accordingly, the expression "C5+ alcohols" is meant to describe a mixture of alcohols having 5 or more carbon atoms.

As used herein the terms "higher alcohols", or the term "HA", refer to alcohols containing at least two carbon atoms, such as ethanol, n-propanol; isopropanol; $C_4$-$C_{20}$ alcohols; C2+ alcohols; etc. Both linear and branched alcohols are included when using the term "higher alcohols" or "HA".

The term "1-HA" refers to primary higher alcohols and the term "2-HA" refers to secondary higher alcohols.

In the HAS process according to the disclosure, a syngas feed stream comprising hydrogen ($H_2$) and carbon oxides (CO alone or a mixture of CO and $CO_2$ gases) is caused to interact with a Cu—Fe-based catalyst composition.

Weight hourly space velocity (WHSV) is defined as the volume of feed stream flowing per unit weight of the catalyst per hour ($cm^3$ $g_{cat}^{-1}$ $h^{-1}$).

Gas hourly space velocity (GHSV) is defined as the volume of feed stream flowing per unit volume of the catalyst per hour ($h^{-1}$).

The Si/Al molar ratio of one or more zeolites refers to the silicon to aluminium bulk molar ratio of said one or more zeolites. Si/Al molar ratio is determined by inductively coupled plasma optical emission spectroscopy.

The zeolite "Z" are referenced into the following description by "Zx", wherein x represents the Si/Al molar ratio of the zeolite. For instance, Z15 represents a zeolite having a Si/Al molar ratio of 15.

As used herein, the term "HZx" refers to a hierarchical zeolite, having a Si/Al molar ratio of x.

As further used herein, the term "KZ$x_p$" refers to a zeolite, having a Si/Al molar ratio of x, and being potassium exchanged. For instance, KMFI-40$_p$ represents an MFI zeolite having a Si/Al molar ratio of 40 and being partially potassium exchanged.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics, examples or embodiments may be combined in any suitable manner, as would be apparent to a person skilled in the art from this disclosure, in one or more embodiments or examples.

The disclosure provides a process for converting syngas to C2+ alcohols, said process comprising the following steps:
  a) providing an installation comprising at least one reactor having one or more catalytic beds;
  b) providing a catalyst composition and one or more acidic materials within said at least one reactor;
  c) providing a feed stream comprising a mixture of $H_2$ and CO;
  d) contacting said feed stream with said catalyst composition and said one or more acidic materials under reaction conditions to provide product stream;
the process is remarkable in that said catalyst composition comprises an active phase comprising CuFe deposited on a carbon-containing support, the total content of iron and copper ranging from 1 to 10 wt. % based on the total weight of the catalyst composition and as determined by inductively coupled plasma optical emission spectroscopy, and the one or more acidic materials being one or more zeolites having a Si/Al molar ratio ranging between 2 and 200 as determined by inductively coupled plasma-optical emission spectroscopy.

Figure 2:
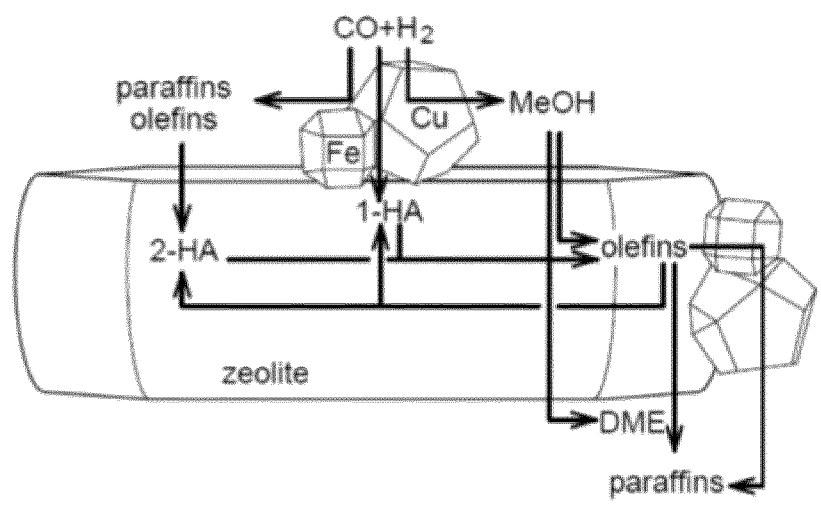
FIG. 2 shows the reaction network for the conversion of syngas to C2+ alcohols over bimetallic CuFe catalyst supported on acidic zeolites.

The disclosure contemplates the combination of the use of catalyst composition and one or more acidic materials based on zeolites in a process for the synthesis of higher alcohols from a syngas feed stream comprising hydrogen and carbon monoxide. The acidity of the zeolite material indeed allows for the hydration of the alkenes that are generated by the CuFe catalyst deposited on a carbon-containing support and thus for the formation of 2-HA. As an independent material, the acidity of the zeolite does not interfere anymore with the key step of higher alcohols synthesis, which is the CO insertion. FIG. 2 provides a schematic visualization of the interplay of the reaction occurring over a CuFe catalyst in the presence of an acidic support.

According to a first embodiment, wherein said at least one reactor comprises a first reactive bed and one or more subsequent reactive beds, one or more subsequent reactive beds being arranged downstream of the first reactive bed, the process is remarkable in that the catalyst composition and the one or more acidic materials are provided in different reactive beds, and in that the catalyst composition is provided in the first reactive bed and the one or more acidic materials are provided in the one or more subsequent reactive beds.

According to a second embodiment, wherein said at least one reactor comprises a first reactive bed and optional one or more subsequent reactive beds, wherein the one or more subsequent reactive beds, when present, are arranged downstream of the first reactive bed, the process is remarkable in that during step (b) a mixture of the catalyst composition and of the one or more acidic materials is provided in the first reactive bed; with preference, one or more acidic materials are provided in the one or more subsequent reactive beds.

The Catalyst Composition

For example, the catalyst composition comprises a copper and iron-based catalyst, wherein the Cu—Fe-based catalyst is on a support to form the catalyst composition. The support provides mechanical support to the catalyst as well as further enhancing the exposure of the syngas feed stream to the active sites of the catalyst.

For example, the carbon-containing support is preferably selected from carbon nanotubes and carbon nanofibers, more preferably the carbon-containing support comprises carbon nanofibers, even more preferably the carbon-containing support is or comprises carbon nanofibers.

For example, the carbon-containing support of the catalyst composition comprises at least 80 wt. % of carbon nanofibers based on the total weight of the carbon-containing support; preferably, at least 90 wt. %; more preferably, at least 95 wt. %; and most preferably 100 wt. %.

When the carbon-containing support is carbon nanofibers, said carbon nanofibers are preferably selected from platelet-type carbon nanofibers and conical platelet-type carbon nanofibers. With preference, the carbon-containing support is or comprises conical platelet-type nanofibers. For example, the carbon-containing support of the catalyst composition comprises at least 60 wt. % of conical platelet-type nanofibers based on the total weight of the carbon-containing support; preferably, at least 80 wt. %; more preferably, at least 90 wt. %; and most preferably 100 wt. %.

For example, the carbon-containing support has a hollow-core structure with an inner diameter of at least 17 nm as determined according to $N_2$ sorption analysis, preferably at least 20 nm, more preferably of at least 25 nm, and even more preferably of at least 30 nm.

For example, the carbon-containing support is conical platelet-type carbon nanofibers being iron-free, i.e. conical platelet-type carbon nanofibers having a content of iron less than 100 ppm based on the total weight of the conical platelet-type carbon nanofibers Iron-free conical platelet-type carbon nanofibers are commercially available and are marketed, for example, by Sigma-Aldrich® under SID 329763680.

With preference, the carbon nanofibers have an aspect ratio D×L ranging from 10 nm×20 μm to 10 nm×200 μm. The average diameter of the carbon nanofibers is ranging from 50 to 200 nm, preferably from 100 to 150 nm. The average pore volume of the carbon nanofibers is ranging from 0.025 $cm^3$ $g^{-1}$ to 0.125 $cm^3$ $g^{-1}$, preferably from 0.05 $cm^3$ $g^{-1}$ to 0.1 $cm^3$ $g^{-1}$. The average pore diameter of the carbon nanofibers is ranging from 50 to 200 Ångström, preferably from 100 to 150 Ångström. The average specific surface area (before deposition of the catalyst and optional calcination) is ranging from 20 to 200 $m^3$ $g^{-1}$, preferably from 20 to 50 $m^3$ $g^{-1}$.

The total metal loading of the catalyst composition, i.e. the Cu—Fe content, is ranging from 1 to 10 wt. % based on the total weight of the catalyst composition and as determined by inductively coupled plasma optical emission spectroscopy. With preference, the total metal loading is ranging from 2.0 to 8.0 wt. % based on the total weight of the catalyst composition as determined by inductively coupled plasma optical emission spectroscopy, preferably ranging from 3.0 to 7.0 wt. %, more preferably from 4.0 to 6.0 wt. %; even more preferably from 4.5 to 5.5 wt. % and most preferably below 5.0 wt. %. In an example, the total metal loading is ranging from 2.0 to 4.9 wt. % based on the total weight of the catalyst composition as determined by inductively coupled plasma optical emission spectroscopy.

The Cu/Fe bulk molar ratio of the catalyst composition is ranging from 0.5/1.0. to 5.0/1.0. With preference, the Cu/Fe bulk molar ratio is ranging from 1.0/1.0 to 4.0/1.0, preferably from 1.2/1.0 to 3.0/1.0; more preferably from 1.5/1.0 to 2.5/1.0; most preferably the Cu/Fe molar ratio is 2.0/1.0.

For example, the Cu particle size is at least 7 nm as determined from the (111) reflection in an XRD pattern using the Scherrer equation, preferably at least 8 nm, more preferably at least 9 nm.

For example, the Cu particle size is at most 35 nm as determined from the (111) reflection in an XRD pattern using the Scherrer equation, preferably at most 30 nm, more preferably at most 25 nm, even more preferably at most 20 nm, most preferably at most 15 nm, and even most preferably at most 11 nm.

For example, the Cu particle size is ranging from 7 to 35 nm as determined from the (111) reflection in an XRD pattern using the Scherrer equation, preferably from 7 to 30 nm, more preferably from 7 to 25 nm, even more preferably from 7 to 20 nm, most preferably from 8 to 15 nm, and even most ranging from 9 to 11 nm.

For example, the catalyst composition further comprises at least one promoter selected from alkali and alkaline earth metal. With preference, at least one promoter is selected from alkali metals, preferably at least one promoter comprises potassium, more preferably at least one promoter is potassium.

For example, the content of the at least one promoter is ranging from 0.001 to 0.5 wt. % based on the total weight of the catalyst composition and as determined by inductively coupled plasma optical emission spectroscopy, preferably from 0.001 to 0.4 wt. %, more preferably from 0.001 to 0.3 wt. %, even more preferably from 0.001 to 0.2 wt. %, most preferably from 0.001 to 0.1 wt. %, even most preferably from 0.002 to 0.05 wt. %, or preferably from 0.004 to 0.03 wt. %, or more preferably from 0.006 to 0.02 wt. %.

The catalyst composition is a calcined catalyst composition having a BET surface area in the range of about 20 $m^2$ $g^{-1}$ to 400 $m^2$ $g^{-1}$ as determined according to $N_2$ sorption analysis.

With preference, the catalyst composition is a reduced catalyst composition as determined by X-ray diffraction wherein the reduced catalyst is devoid of iron oxide.

Method to Prepare the Catalyst Composition

A method to produce a catalyst composition used in the process according to the first aspect is also reported. The method is remarkable in that it comprises the following steps:
 i. Co-precipitating iron and copper together, optionally with at least one promoter, and re-dissolving them with a complexing agent to form a mixture;
 ii. Depositing the mixture on the carbon-containing support to obtain a slurry;

iii. Drying the slurry and activating the dried material through reduction to obtain a reduced catalyst composition;

iv. Optionally calcining the dried catalyst composition to obtain a calcined catalyst composition.

As it is clear to the person skilled in the art, the method to produce a catalyst composition is preferably a sol-gel method. With preference, at least one promoter is an alkali promoter.

The complexing agent is selected from citric acid, ethylenediaminetetraacetic acid (EDTA), tartaric acid, glycolic acid, oxalic acid, glycine, urea and ethylene glycol; with preference, the complexing agent is citric acid.

With preference, step i) of co-precipitating iron and copper together with the promoter to form a mixture comprises the following sub-steps:

Preparing a solution of copper precursor and iron precursor with water;

Adding $NH_4OH$ to the solution to form a precipitate and dissolving the recovered solid in a complexing agent solution, preferably a citric acid solution;

Adding a desired amount of an alkali carbonate, preferably potassium carbonate.

Optionally, adjusting the pH of the mixture to value preferably between 2 and 5, more preferably between 3 and 5, and most preferably between 3 and 4.

With preference, the activation step iii) is performed in diluted $H_2$ at a temperature above 600 K.

With preference, said precursors are nitrate derivatives, chloride derivatives and/or acetate derivatives. More preferentially, said precursors are nitrate derivatives, such as copper (II) nitrate hydrate and iron (III) nitrate hydrate.

The catalyst composition can be prepared as described in H. T. Luk et al. in "*Role of Carbonaceous Supports and Potassium Promoter on Higher Alcohols Synthesis over Copper-Iron Catalysts*", ACS Catal. 8 (2018) 9604-9618; which is incorporated herein by reference.

The One or More Acidic Materials

The one or more acidic materials that are combined with the catalyst composition are one or more zeolites having a Si/Al molar ratio ranging between 2 and 200 as determined by inductively coupled plasma-optical emission spectroscopy. The one or more zeolites are selected from MFI, FAU, MOR, FER, BEA, TON, MTT, OFF families, or any mixture thereof, preferably from the MFI, MOR and BEA families, more preferably from the MFI and MOR families.

With preference, the one or more zeolites from the MFI family are selected from ZSM-5, silicalites, boralite C, or TS-I. More preferentially, the zeolite from the MFI family is ZSM-5 or silicalites. The zeolite from the FAU family is, more preferentially, Y zeolite. The zeolite from the MOR family is, more preferentially, mordenite. The zeolite from the FER family is, more preferentially, ferrierite. The zeolite from the BEA family is, more preferentially, zeolite beta. The zeolite from the TON family is, more preferentially, ZSM-22. The zeolite from the MTT family is, more preferentially, ZSM-23. The zeolite from the OFF family is, more preferentially, offretite.

With preference, the one or more zeolites comprise at least one 10-membered ring channel and/or at least one 12-membered ring channel.

With preference, the one or more zeolites have a Si/Al molar ratio ranging between 2 and 100 as determined by inductively coupled plasma-optical emission spectroscopy, preferably between 5 and 90, more preferably between 10 and 70, even more preferably between 30 and 60, most preferably between 40 and 50; or between 100 and 200 as determined by inductively coupled plasma-optical emission spectroscopy, preferably between 110 and 190, more preferably between 120 and 180, even more preferably between 140 and 160.

The density of Brønsted-acid sites ($C_{BAS}$) has been determined by Fourier transform infrared (FTIR) spectroscopy of adsorbed pyridine. By coherence with the Si/Al molar ratio, acidic zeolite supports with a Si/Al molar ratio ranging between 2 and 200 have a $C_{BAS}$ comprised between 50 $\mu$mol $g^{-1}$ and 700 $\mu$mol $g^{-1}$.

With preference, the one or more zeolites have a density of Brønsted-acid sites ranging from 5 $\mu$mol $g^{-1}$ to 700 $\mu$mol $g^{-1}$ as determined by FTIR spectroscopy of adsorbed pyridine, more preferably from 40 $\mu$mol $g^{-1}$ to 600 $\mu$mol $g^{-1}$, even more preferably from 50 $\mu$mol $g^{-1}$ to 500 $\mu$mol $g^{-1}$.

With preference, the one or more zeolites have a density of Brønsted-acid sites of less than 200 $\mu$mol $g^{-1}$ as determined by FTIR spectroscopy of adsorbed pyridine, more preferably of less than 150 $\mu$mol $g^{-1}$, even more preferably of less than 100 $\mu$mol $g^{-1}$; and/or of at least 5 $\mu$mol $g^{-1}$, preferentially of at least 25 $\mu$mol $g^{-1}$, more preferentially of at least 40 $\mu$mol $g^{-1}$.

The density of Lewis-acid sites ($C_{LAS}$) has been determined by FTIR spectroscopy of adsorbed pyridine. The trend follows the Si/Al molar ratio and the density of Brønsted-acid sites ($C_{BAS}$) of the zeolite carrier. An acidic zeolite has a $C_{LA}S$ ranging between 4 $\mu$mol $g^{-1}$ and 250 $\mu$mol $g^{-1}$.

With preference, the one or more zeolites have a density of Lewis-acid sites ranging from 4 $\mu$mol $g^{-1}$ to 250 $\mu$mol $g^{-1}$ as determined by FTIR spectroscopy of adsorbed pyridine, more preferably from 15 $\mu$mol $g^{-1}$ to 150 $\mu$mol $g^{-1}$.

The one or more zeolites have a density of Lewis-acid sites of less than 50 $\mu$mol $g^{-1}$ as determined by FTIR spectroscopy of adsorbed pyridine, preferably of less than 40 $\mu$mol $g^{-1}$; more preferably of less than 15 $\mu$mol $g^{-1}$; and/or of at least 4 $\mu$mol $g^{-1}$, preferentially of at least 8 $\mu$mol $g^{-1}$.

With preference, the one or more zeolites are partially ion-exchanged with an alkali metal-based ion, preferably with potassium. This allows for the reduction of the acidity of the one or more zeolites.

With preference, the one or more zeolites have a surface area comprised between 10 $m^2$ $g^{-1}$ and 600 $m^2$ $g^{-1}$ as determined by the BET method, preferably comprised between 250 $m^2$ $g^{-1}$ and 450 $m^2$ $g^{-1}$, more preferably comprised between 300 $m^2$ $g^{-1}$ and 400 $m^2$ $g^{-1}$.

Optionally, a desilication step has been performed on the zeolite, in order to introduce mesoporosity to the support. This surface area thus increases to above 400 $m^2$ $g^{-1}$ as determined by the BET method and the pore volume also increase to above 0.40 $cm^3$ $g^{-1}$. The desilication step allows for obtaining a zeolite that is called "hierarchical zeolite".

With preference, the one or more zeolites have a pore volume comprised between 0.15 $cm^3/g$ and 1.25 $cm^3$ $g^{-1}$, as determined by $N_2$ sorption analysis, preferably between 0.18 $cm^3$ $g^{-1}$ and 1.00 $cm^3$ $g^{-1}$, more preferably between 0.16 $cm^3$ $g^{-1}$ and 0.50 $cm^3$ $g^{-1}$, even more preferably between 0.20 $cm^3$ $g^{-1}$ and 0.30 $cm^3$ $g^{-1}$.

With preference, the one or more zeolites have a crystal size comprised between 20 nm and 10 $\mu$m as determined by Scanning Electron Microscopy (SEM), preferably between 50 nm and 8 $\mu$m, more preferably between 70 nm and 5 $\mu$m, and most preferably between 100 nm and 2 $\mu$m.

The HAS Process

With preference, the HAS process is carried out in a gaseous phase and is carried out in a continuous-flow reactor.

With preference, the weight ratio of the catalyst composition over the acidic material is ranging between 0.1 and 10, preferably between 0.2 and 5, more preferably between 0.3 and 3, most preferably between 0.5 and 2.

With preference, the syngas feed stream has a molar $H_2$/carbon oxides ratio ranging from 0.5/1 to 12.0/1, more preferably ranging from 0.5/1 to 10.0/1, even more preferably ranging from 0.5/1 to 8.0/1, most preferably ranging from 0.5/1 to 6.0/1, even most preferably ranging from 0.7/1 to 3.0/1, or more preferably ranging from 1.0/1 to 2.5/1, or even more preferably ranging from 1.2/1 to 2.2/1, or even most preferably is 2.0/1; wherein the carbon oxide comprises CO and/or $CO_2$, preferably a mixture of CO and $CO_2$.

With preference, the syngas feed stream has a molar $H_2$/CO ratio ranging from 0.5/1 to 12.0/1, more preferably ranging from 0.5/1 to 10.0/1, even more preferably ranging from 0.5/1 to 8.0/1, most preferably ranging from 0.5/1 to 4.0/1, even most preferably ranging from 0.7/1 to 3.0/1.

With preference, the syngas feed stream comprises at least 5 mol % of CO based on the total molar content of the syngas feed, more preferably at least 15 mol %, even more preferably at least 20 mol %.

With preference, the syngas feed stream comprises at least 20 mol % of $H_2$ based on the total molar content of the syngas feed, more preferably at least 25 mol %, even more preferably at least 30 mol %.

With preference, the syngas feed stream comprises a mixture of carbon monoxide (CO) and of carbon dioxide ($CO_2$); or the syngas feed stream is devoid of carbon dioxide ($CO_2$).

With preference, the syngas feed stream comprises a mixture of carbon monoxide (CO) and of carbon dioxide ($CO_2$) with the content of $CO_2$ being at most 10 mol % based on the total molar content of the syngas feed, more preferably ranging from 0.5 to 8.0 mol %, even more preferably ranging from 1.0 to 6.0 mol %, and most preferably ranging from 3.0 to 5.0 mol %.

With preference, the process is carried out during more than 100 hours without replacement or reactivation of the catalyst composition, preferably more than 500 hours.

With preference, the process further comprises a step (e) of recovering the product stream containing higher alcohols. This step (e) can be carried out by distillation.

In an example, the process is carried out in a fixed bed or fluidised bed reactor comprising at least one catalytic bed. Such reactors are well-known from the person skilled in the art and for instance described in EP2257366 or in U.S. Pat. No. 7,279,138.

The First Reactive Bed

In the first embodiment, the first reactive bed only comprises the catalyst composition.

In the second embodiment, the process is carried out in a mixed-bed configured reactor. Advantageously, the reactive bed in which the catalyst composition and the one or more acidic materials are mixed during step (b) is a first reactive mixed-bed, and the reactor further comprises at least one reactive bed.

The mixing of the catalyst composition is performed by physical mixing at room temperature (i.e. between 20° C. and 25° C.).

Whatever is the embodiment selected the reaction conditions in the first reactive bed can be defined as follows:

With preference, the reaction conditions comprise a reaction temperature ranging from 443 K (169.85° C.) to 653 K (379.85° C.), more preferably from 493 K (219.85° C.) to 553 K (279.85° C.), even more preferably from 513 K (239.85° C.) to 548 K (274.85° C.), and most preferably at a reaction temperature of 543 K (269.85° C.).

With preference, the reaction conditions comprise a reaction pressure range ranging from 1 MPa to 10 MPa, more preferably from 2 to 9 MPa, even more preferably from 3 to 7 MPa, most preferably from 4 to 6 MPa, and even most preferably at a reaction pressure of 5 MPa.

With preference, the reaction conditions comprise a weight hourly space velocity (WHSV) ranging from 500 $cm^3\ g_{cat}^{-1}\ h^{-1}$ to 48000 $cm^3\ g_{cat}^{-1}\ h^{-1}$, more preferably from 6000 $cm^3\ g_{cat}^{-1}\ h^{-1}$ to 34000 $cm^3\ g_{cat}^{-1}\ h^{-1}$, even more preferably from 8000 $cm^3\ g_{cat}^{-1}\ h^{-1}$ to 32000 $cm^3\ g_{cat}^{-1}\ h^{-1}$; most preferably from 14000 $cm^3\ g_{cat}^{-1}\ h^{-1}$ to 28000 $cm^3\ g_{cat}^{-1}\ h^{-1}$, even most preferably from 16000 $cm^3\ g_{cat}^{-1}\ h^{-1}$ to 24000 $cm^3\ g_{cat}^{-1}\ h^{-1}$.

With preference, the reaction conditions comprise a weight hourly space velocity (WHSV) of at least 500 $cm^3\ g_{cat}^{-1}\ h^{-1}$, more preferably at least 1,000 $cm^3\ g_{cat}^{-1}\ h^{-1}$, even more preferably of at least 2,000 $cm^3\ g_{cat}^{-1}\ h^{-1}$, most preferably at least 4,000 $cm^3\ g_{cat}^{-1}\ h^{-1}$, and even most preferably at least 8,000 $cm^3\ g_{cat}^{-1}\ h^{-1}$.

Preferably, the reaction conditions comprise a weight hourly space velocity of at most 48,000 $cm^3\ g_{cat}^{-1}\ h^{-1}$, preferably at most 34,000 $cm^3\ g_{cat}^{-1}\ h^{-1}$, more preferably of at most 32,000 $cm^3\ g_{cat}^{-1}\ h^{-1}$.

The One or More Subsequent Reactive Beds

The one or more subsequent reactive beds comprising one or more acidic materials can be in the same reactor than the first reactive bed (multiple reactive beds in the same reactor) or in one or more subsequent reactors. In case, the one or more subsequent reactive beds are located in the same reactor than the first reactive bed, the reaction conditions (temperature and pressure) within the said reactor will be selected to be according to the first reactive bed.

In case the one or more subsequent reactive beds are located in one or more subsequent reactors, the reaction conditions (temperature and pressure) in the one or more subsequent reactors are preferably selected to be different from the first reactor containing the first reactive bed.

In both examples, the one or more reactive beds comprise one or more acidic materials being one or more zeolites.

With preference, the process is carried out in a dual-bed configured reactor.

With preference, the first and one or more subsequent reactive beds are spatially separated before step (c).

Advantageously, the process is carried out in a reactor comprising at least two reactive beds.

With preference, the first reactive bed and the one or more subsequent reactive beds are disposed in series within the reactor.

With preference, the reaction conditions comprise a reaction temperature ranging from 373 K (99.85° C.) to 773 K (499.85° C.), more preferably from 393 K (119.85° C.) to 673 K (399.85° C.).

With preference, the reaction conditions comprise a reaction temperature of at least 373 K (99.95° C.), more preferentially of at least 398 K (124.85° C.), even more preferentially of at least 403 K (129.85° C.), most preferably of at least 418 K (139.85° C.) and even most preferably of at least 423 K (149.85° C.).

With preference, the reaction conditions comprise a reaction temperature of at most 773 K (499.85° C.), more preferentially of at most 573 K (299.85° C.).

With preference, the reaction conditions of the one or more subsequent reactive beds comprise a reaction temperature that is the same or different as the reaction temperature in the first reactive bed. With preference, the reaction conditions of the one or more subsequent reactive beds comprise a reaction pressure that is different or the same as in the first reactive bed.

With preference, the reaction conditions comprise a reaction pressure ranging from 0.1 MPa to 10.0 MPa, more preferably ranging from 0.5 MPa to 8.0 MPa, even more preferably ranging from 1.0 MPa to 7.0 MPa.

With preference, the reaction conditions comprise a reaction pressure range of at least 1.0 MPa, more preferentially of at least 1.5 MPa, even more preferably of at least 2.0 MPa.

The reaction conditions comprise a reaction pressure of at most 10.0 MPa, more preferably of at most 6.5 MPa, even more preferably of at most 6.0 MPa.

With preference, the reaction conditions comprise a weight hourly space velocity (WHSV) ranging from 500 $cm^3 \, g_{cat}^{-1} \, h^{-1}$ to 50,000 $cm^3 \, g_{cat}^{-1} \, h^{-1}$, more preferably from 2,000 $cm^3 \, g_{cat}^{-1} \, h^{-1}$ to 40,000 $cm^3 \, g_{cat}^{-1} \, h^{-1}$, even more preferably from 4,000 $cm^3 \, g_{cat}^{-1} \, h^{-1}$ to 35,000 $cm^3 \, g_{cat}^{-1} \, h^{-1}$, most preferably from 6,000 $cm^3 \, g_{cat}^{-1} \, h^{-1}$ to 32,000 $cm^3 \, g_{cat}^{-1} \, h^{-1}$.

With preference, the reaction conditions comprise a weight hourly space velocity (WHSV) of at least 2,000 $cm^3 \, g_{cat}^{-1} \, h^{-1}$, more preferably at least 4,000 $cm^3 \, g_{cat}^{-1} \, h^{-1}$, even more preferably of at least 6,000 $cm^3 \, g_{cat}^{-1} \, h^{-1}$, most preferably at least 8,000 $cm^3 \, g_{cat}^{-1} \, h^{-1}$.

With preference, the reaction conditions comprise a weight hourly space velocity (WHSV) of at most 50,000 $cm^3 \, g_{cat}^{-1} \, h^{-1}$, more preferably at most 40,000 $cm^3 \, g_{cat}^{-1} \, h^{-1}$, even more preferably at most 35,000 $cm^3 \, g_{cat}^{-1} \, h^{-1}$, most preferably at most 32,000 $cm^3 \, g_{cat}^{-1} \, h^{-1}$.

For example, the catalyst composition is a catalyst comprising KCuFe deposited on a carbon-containing support being carbon nanofibers, the total content of iron and copper ranging from 1 to 10 wt. % based on the total weight of the catalyst composition and as determined by inductively coupled plasma optical emission spectroscopy; and the one or more acidic materials are one or more MFI zeolites having a Si/Al molar ratio ranging between 2 and 100 as determined by inductively coupled plasma-optical emission spectroscopy. At a CO conversion rate of 4%, the selectivity to C2+ alcohols is at least 30% and the selectivity into 2-HA is at least 10%. The selectivity into methanol is less than 3%. The selectivity into carbon dioxide is less than 15%.

For example, the catalyst composition is a catalyst comprising KCuFe deposited on a carbon-containing support being carbon nanofibers, the total content of iron and copper ranging from 1 to 10 wt. % based on the total weight of the catalyst composition and as determined by inductively coupled plasma optical emission spectroscopy; and the one or more acidic materials are one or more MFI zeolites having a Si/Al molar ratio ranging between 100 and 200 as determined by inductively coupled plasma-optical emission spectroscopy. At a CO conversion rate of 4%, the selectivity to C2+ alcohols is at least 40%. The selectivity into methanol is less than 3%. The selectivity into carbon dioxide is less than 20%.

For example, the catalyst composition is a catalyst comprising KCuFe deposited on a carbon-containing support being carbon nanofibers, the total content of iron and copper ranging from 1 to 10 wt. % based on the total weight of the catalyst composition and as determined by inductively coupled plasma optical emission spectroscopy; and the one or more acidic materials are one or more MFI zeolites partially exchanged with potassium and having a Si/Al molar ratio ranging between 2 and 100 as determined by inductively coupled plasma-optical emission spectroscopy. At a CO conversion rate of 4%, the selectivity to C2+ alcohols is at least 45%, the selectivity into methanol is less than 3% and the selectivity into carbon dioxide is less than 10%. At a CO conversion rate of 8%, the selectivity into C2+ alcohol is at least 45%, the selectivity into methanol is 0% and the selectivity into carbon dioxide is less than 10%.

For example, the catalyst composition is a catalyst comprising KCuFe deposited on a carbon-containing support being carbon nanofibers, the total content of iron and copper ranging from 1 to 10 wt. % based on the total weight of the catalyst composition and as determined by inductively coupled plasma optical emission spectroscopy; and the one or more acidic materials are one or more BEA zeolites having a Si/Al molar ratio ranging between 2 and 100 as determined by inductively coupled plasma-optical emission spectroscopy. At a CO conversion rate of 4%, the selectivity to C2+ alcohols is at least 45%, the selectivity into methanol is less than 3% and the selectivity into carbon dioxide is less than 15%.

For example, the catalyst composition is a catalyst comprising KCuFe deposited on a carbon-containing support being carbon nanofibers, the total content of iron and copper ranging from 1 to 10 wt. % based on the total weight of the catalyst composition and as determined by inductively coupled plasma optical emission spectroscopy; and the one or more acidic materials are one or more MOR zeolites having a Si/Al molar ratio ranging between 100 and 200 as determined by inductively coupled plasma-optical emission spectroscopy. At a CO conversion rate of 4%, the selectivity to C2+ alcohols is at least 50%, the selectivity into methanol is less than 3% and the selectivity into carbon dioxide is less than 15%.

Test and Determination Methods

Inductively coupled plasma optical emission spectroscopy (ICP-OES) has been applied to determine the contents of K, Si and Al in the catalyst composition. To achieve this analytical technique, Horiba Ultra 2 instrument equipped with a photomultiplier tube detector was used.

X-ray fluorescence spectroscopy (XRF) was performed using an Orbis Micro-EDXRF spectrometer equipped with an Rh source operated at 35 kV and 500 μA and a silicon drift detector to obtain the molar Cu/Fe ratio and CuFe loading of the supported catalysts.

$N_2$ sorption at 77 K was measured in a Micromeritics TriStar II instrument after degassing the samples at 573 K under vacuum for 3 h.

The volume of the pores of the one or more zeolites was determined from the volume measured at the equilibrium between the gas pressure (p) and the saturation pressure ($p_0$).

The surface area of supports and catalysts was calculated by applying the BET method.

Powder X-ray diffraction (XRD) was conducted using a PANalytical X'Pert Pro-MPD diffractometer with Ni-filtered Cu Kα radiation (l=0.1541 nm), acquiring data in the 10-70° 2θ range with an angular step size of 0.033° and a counting time of 8 s per step.

The size of metallic copper crystallites was estimated by using the Scherrer equation.

The size and location of metallic copper and iron particles were determined by high-resolution transmission electron microscopy (HRTEM) and scanning transmission electron microscopy coupled to energy-dispersive X-ray spectroscopy (STEM-EDX).

Temperature-programmed reduction with hydrogen ($H_2$-TPR) was carried out using a Micromeritics Autochem 2950 HP unit equipped with a thermal conductivity detector and coupled to a Pfeiffer Vacuum Omnistar™ GSD-320 quadrupole mass spectrometer. 0.050 g of the sample was dried in an Ar flow of 20 cm$^3$ STP min$^{-1}$ at 423 K for 1 h and cooled to 323 K before the temperature was ramped up to 973 K (10 K min$^{-1}$) in a 5 vol % $H_2$/Ar flow of 20 cm$^3$ STP min$^{-1}$ for the analysis.

Fourier transform infrared spectroscopy (FTIR) of adsorbed pyridine was conducted in a Bruker IFS 66 spectrometer. The samples were pressed into self-supporting wafers of ca. 1 cm$^2$ and degassed under vacuum (10-3 mbar) at 473 K for 4 h, followed by pyridine adsorption at room temperature. Gaseous and weakly adsorbed molecules were removed by evacuation at 473 K for 30 min. Spectra were acquired collecting 32 scans in the range of 650-4000 cm$^{-1}$ with a resolution of 4 cm$^{-1}$.

High-resolution transmission electron microscopy (HR-TEM) and scanning transmission electron microscopy coupled to energy-dispersive X-ray spectroscopy (STEM-EDX) were conducted in an FEI Talos F200A instrument equipped with a high-brightness field emission gun, a high-angle annular dark-field (HAADF) detector, and a large collection angle EDX detector, operated at 200 kV. Catalyst powders were dispersed on nickel grids coated with a continuous carbon film.

Thermogravimetric analysis (TGA) has been used to check the amount of coke deposition on the used catalyst. TGA was carried out in a Linseis DSC PT1600 instrument. The amount of coke was determined by registering the weight loss curve in the temperature range of 303-1173 K at a rate of 10 K min$^{-1}$ under 25 cm$^3$ STP min$^{-1}$ of airflow.

Gas chromatography experiments were carried out to determine quantitatively the selectivity of the reaction. The gas chromatograph comprised two columns (ShinCarbon ST and PoraPLOT Q PT), a thermal conductivity detector (TCD) and a flame ionization detector (FID) and was operated with the ChemStation software by Agilent.

Scanning Electron Microscopy (SEM) has been used to determine the crystal size of the one or more zeolites.

The conversion rate of carbon monoxide ($X_{CO}$) was determined according to formula (1):

$$X_{CO} = \frac{n_{CO,in} - n_{CO,out}}{n_{CO,in}} \cdot 100\% \qquad (1)$$

wherein $n_{CO,in}$ and $n_{CO,out}$ are the molar flows of CO (expressed in mmol/h) at the inlet and outlet of the reactor, respectively.

The selectivity to product i ($S_i$) was calculated using equation (2)

$$s_I = \frac{n_{i,out} N_{c,i}}{\sum n_{i,out} N_{c,i}} \cdot 100\% \qquad (2)$$

wherein $n_{i,out}$ and $N_{c,i}$ are the molar flow of product i at the outlet of the reactor and the number of carbon atoms in product i, respectively. The selectivity to C2+ alcohols was obtained summing the individual selectivities to alcohols with 2 or more carbon atoms, while that to hydrocarbons summing the individual selectivities to hydrocarbon with 1 or more carbon atoms.

The space-time yield of HA ($STY_{HA}$) expressed in $g_{HA}$ $g_{cat}^{-1}$ h$^{-1}$ was calculated using equations (3):

$$STY_{HA} = \sum S_{j,HA} MW_{j,HA} \frac{X_{CO} n_{CO,in}}{m_{cat}} \qquad (3)$$

wherein $m_{cat}$ is the mass of the catalyst and $MW_{j,HA}$ is the molecular weight of higher alcohols (i.e. C2+ alcohols) containing j carbon atoms.

The carbon balance was determined according to equation (4) and was always higher than 95%.

$$\varepsilon_C = \frac{n_{CO,in} - \sum n_{i,out} N_{c,i}}{n_{CO,in}} \cdot 100\% \qquad (4)$$

EXAMPLES

The embodiments or examples of the present disclosure will be better understood by looking at the different examples below.

Various zeolites were used as acidic material in combination with CuFe catalysts.

Example 1: CuFe Catalysts Preparation

Bulk Catalyst

A bulk Cu—Fe catalyst with nominal molar Cu/Fe=2 was prepared by co-precipitation using $Na_2CO_3$ as the precipitating agent. $Cu(NO_3)_2 \cdot 3H_2O$ (5.283 g, Aldrich Fine Chemicals, 98-103%) and $Fe(NO_3)_3 \cdot 9H_2O$ (4.406 g, Aldrich Fine Chemicals, >98%) were dissolved simultaneously in deionised water (65.6 cm$^3$) yielding a solution with a total metals concentration of 0.5 M. The mixture was magnetically stirred at 343 K while adding a 0.5 M $Na_2CO_3$ solution (81-83 cm$^3$, 2 cm$^3$ min$^{-1}$) to reach a pH of 8. The slurry obtained was aged for 3 h, washed with water (3 dm$^3$), dried at 343 K, calcined at 723 K, and reduced in a 10 vol. % $H_2$/He flow of 20 cm$^3$ min$^{-1}$ for 4 h at 673 K (ramp rate=3 K min$^{-1}$).

Supported Catalysts

Supported Cu—Fe catalysts with nominal molar Cu/Fe molar ratios of 1, 2, 3, or 5, and a Cu—Fe loading of 5 wt. % were prepared by a sol-gel method (SG). K was added as a promoter to the materials with Cu/Fe=2 in a nominal molar K/Cu—Fe molar ratio of 0.005, 0.01, or 0.1. Conical platelet-type CNF (Aldrich-Fine Chemicals, Fe content<100 ppm, denoted as CNF), platelet-type CNF (ABCR, >98%, denoted as CNF$_p$), multi-walled carbon nanotubes (ABCR, 95%, outer diameter=20-30 nm, denoted as CNT), and activated carbon (ACROS Organics Co., Ltd., denoted as AC) were used as carriers as received.

$Cu(NO_3)_2 \cdot 3H_2O$ (2.130-3.404 g) and $Fe(NO_3)_3 \cdot 9H_2O$ (1.138-3.562 g) were dissolved in deionised water (11.5 cm$^3$) under magnetic stirring. With the addition of 4-5 drops of $NH_4OH$ (Acros Organics, 25 wt. % aqueous solution), a dark green precipitate was formed. A citric acid (Sigma-Aldrich, >95%) solution (1.30-1.36 g in 3 cm$^3$ of water, corresponding to a molar citric acid/Cu—Fe ratio of 0.4) was then added under magnetic stirring to re-dissolve the solid. When desired, an adequate amount of $K_2CO_3$ solution (0.006-0.12 g in 1 cm$^3$ of water) was incorporated. The pH of the solution was adjusted to 3.5 adding few drops of formic acid (Merck product, 98-100%) and NH$_4$OH. An aliquot of this final mixture was added to 2.0 g of support to achieve the desired metals loading. The slurry was magnetically stirred for 6 h at 338 K and dried in air at the same temperature overnight. The obtained solid was sieved to attain a 0.05-0.12 mm fraction, which was activated by reduction in a 10 vol. % H$_2$/He flow of 20 cm$^3$ min$^{-1}$ for 4 h at 673 K (3 K min$^{-1}$).

These catalysts were coded combining information on the support (abbreviation), the molar Cu/Fe ratio, and the molar relative amount of K in the catalyst (if relevant), e.g., CNF-2-0.01. A portion of the CNF-2 catalyst was calcined in air for 3 h at 573 K (5 K min$^{-1}$) prior to the reduction step (denoted as CNF-2-C).

The sol-gel method was applied to prepare additional catalysts supported on CNF with a nominal Cu/Fe=2 through sequential addition of the metals, i.e., Fe/Cu/CNF-2 (Cu incorporated prior to Fe), K/Cu-Fe/CNF-2-0.005 (K added after the simultaneous deposition of Cu and Fe), Fe/Cu-K/CNF-2-0.005 (Fe added after the simultaneous incorporation of Cu and K), and Cu—Fe/K/CNF-2-0.005 (Cu and Fe added simultaneously after K deposition). The amount of citric acid used during the individual deposition of Cu or Fe was adjusted to attain the same molar ratio as upon the one-pot deposition of the two metals. The solids were reduced after each incorporation of Cu and/or Fe applying the conditions detailed above.

Supported catalysts with nominal molar Cu/Fe=2 and Cu—Fe loading of 5 wt. % and CNF as the carrier were alternatively prepared by a wet deposition-reduction approach using NaBH$_4$ as the reducing agent (denoted as CR-CNF-2) and by deposition-precipitation using Na$_2$CO$_3$ as the precipitating agent (denoted as DP-CNF-2). Along the former route, Cu(NO$_3$)$_2$.3H$_2$O (0.2773 g) and Fe(NO$_3$)$_3$.9H$_2$O (0.2318 g) were dissolved in deionised water (172 cm$^3$) to attain a total concentration of metals of 0.01 M. 2 g of CNF were added to this aqueous solution and the mixture was magnetically stirred at 298 K for 1 h. Afterwards, a 0.5 M NaBH$_4$ solution was introduced (51 cm$^3$, 2 cm$^3$ min$^{-1}$) and the mixture was kept under stirring overnight at 298 K. The solid was recovered by filtration, washed with water (3 dm$^3$), and dried in vacuum overnight at 343 K. DP-CNF-2 was prepared by dissolving the same amounts of salts of metals in 86 cm$^3$ of water, leading to a total concentration of metals of 0.02 M. 2 g of CNF were introduced to this solution and the mixture was refluxed under stirring at 333 K for 1 h. Thereafter, a 0.04 M Na$_2$CO$_3$ solution was added (55 cm$^3$, 2 cm$^3$ min$^{-1}$) to the mixture until a pH of 8 was attained. The slurry was aged at the same temperature for 3 h. The solid was recovered by filtration, washed with water (3 dm$^3$), dried overnight in the air at 333 K, calcined in air for 4 h at 723 K (5 K min$^{-1}$), and finally reduced under the aforementioned conditions.

Performance of the catalysts tested is given in FIG. 1a.

Example 2: Effect of K Promotion on CNF-Supported Cu—Fe Catalysts

The impact of potassium as a promoter was studied on CNF-2. Three materials were prepared including different amounts of the alkali metal upon deposition of Cu and Fe so to reach nominal K/CuFe ratios of 0.005, 0.01 and 0.1. In addition, since the K loading is very small and falls below the detection limit of many characterisation techniques, it was attempted to gather insights into its role by varying the location and contact of this promoter with the active metals tailoring the synthesis method.

Hence, K was incorporated prior to or after the simultaneous deposition of Cu and Fe (CuFe/K/CNF-2-0.005 and K/CuFe/CNF-2-0.005) and along with Cu prior to Fe addition (Fe/CuK/CNF-2-0.005). The measured Cu/Fe ratio and Cu—Fe loading of the reduced catalysts were close to the nominal values (see Table 1), but the K loadings were systematically lower than expected, likely due to the presence of moisture in K$_2$CO$_3$.

When K was introduced prior to or after the active metals, the particles of both Cu and Fe had larger dimensions than in the case of CNF-2-0.005 and CNF-2-0.01, but Cu remained less aggregated and Fe formed larger particles with respect to CNF-2-0.1 (see Table 1). By simultaneously incorporating K and Cu before Fe, both active metals were highly dispersed.

TABLE 1

Characterization data for CNF-supported KCuFe catalysts prepared with different K loadings and by different synthesis methods in reduced form.

| Catalysts | Cu-Fe content[a] [wt. %] | Bulk molar K/Cu-Fe ratio | Bulk molar Cu/Fe ratio[a] | Surface molar Cu/Fe ratio[b,c] | $S_{BET}$[c,d] [m$^2$ g$^{-1}$] | $V_{pore}$[c,e] [cm$^3$ g$^{-1}$] | $d_{Cu}$[c,f] [nm] |
|---|---|---|---|---|---|---|---|
| CNF-2-0.1 | 5.0 | 0.07 | 1.98/1 | — | 24 (0.4) | 0.09 (—) | 20.9 (9.8) |
| CNF-2-0.01 | 4.8 | 0.007 | 2.08/1 | — | 24 (4) | 0.09 (—) | 11.0 (8.8) |
| CNF-2-0.005 | 4.9 | 0.003 | 2.07/1 | 1.2 (0.3) | 24 (7) | 0.09 (0.02) | 11.4 (9.9) |
| K/CuFe/CNF-2-0.005 | 4.9 | 0.004 | 1.91/1 | 0.6 | 31 (28) | 0.11 (0.10) | 15.8 (14.7) |
| CuFe/K/CNF-2-0.005 | 5.0 | 0.003 | 1.91/1 | — | 29 (12) | 0.10 (0.03) | 19.3 (11.4) |
| Fe/CuK/CNF-2-0.005 | 4.4 | 0.004 | 2.02/1 | — | 28 (22) | 0.12 (0.10) | — |

[a]ICP-OES.

[b]XPS.

[c]Data for the used samples in brackets.

[d]BET method.

[e]t-plot method.

[f]Size of Cu determined by Scherrer equation based on the Cu (111) crystalline phase.

The product distributions attained for these catalysts at the same conversion level are given in FIG. 1c and Table 2.

towards methanol and alkanes. The HA selectivity reached 37% over CNF-2-0.005 and matched the selectivity of the

TABLE 2

Performance data for the catalysts investigated.

| Catalyst | WHSV (cm$^3$ g$_{cat}^{-1}$ h$^{-1}$) | STY$_{HA[ROH]}$[a] (g$_{HA}$ g$_{cat}^{-1}$ h$^{-1}$) | X$_{CO}$ (%) | S$_{MeOH}$ (%) | S$_{HA}$ (%) | S$_{HC=}$ (%) | S$_{HC—}$ (%) | S$_{CO2}$ (%) |
|---|---|---|---|---|---|---|---|---|
| CNF-2-0.1 | 4,000 | 0.02 [0.02] | 12 | 0.2 | 13 | 15 | 12 | 60 |
|  | 8,000 | 0.03 [0.04] | 8 | 1 | 15 | 12 | 10 | 61 |
| CNF-2-0.01 | 4,000 | 0.09 [0.11] | 44 | 3 | 15 | 12 | 17 | 53 |
|  | 16,000 | 0.22 [0.25] | 8 | 5 | 47 | 15 | 14 | 18 |
| CNF-2-0.005 | 4,000 | 0.18 [0.26] | 70 | 6 | 19 | 7 | 48 | 20 |
|  | 32,000 | 0.28 [0.42] | 8 | 13 | 37 | 20 | 19 | 11 |
| CuFe/K/CNF-2-0.005 | 4,000 | 0.15 [0.21] | 61 | 5 | 16 | 12 | 31 | 36 |
|  | 20,000 | 0.21 [0.28] | 8 | 9 | 30 | 20 | 23 | 18 |
| Fe/CuK/CNF-2-0.005 | 4,000 | 0.01 [0.02] | 8 | 5 | 11 | 16 | 46 | 21 |
| K/CuFe/CNF-2-0.005 | 4,000 | 0.01 [0.02] | 8 | 5 | 9 | 16 | 33 | 37 |
| KCuFe/SiO$_2$-BM[b] | 6,000 | 0.23 [0.32] | 53 | 23 | 38 | 11 |  | 28 |
| CuFeMg[c] | 2,000 | 0.19 [0.28] | 57 | 16 | 33 | 39 |  | 12 |
| Cu$_2$Fe-3DOM[d] | 2,000 | 0.15 [0.19] | 58 | 4 | 26 | 58 |  | 12 |

[a]Reaction conditions: 543 K, 5 MPa, and molar H$_2$/CO = 2. HA = higher alcohols, MeOH = methanol, HC= = alkenes, and HC— = alkanes.
[b]Reference catalyst, data retrieved from Fuel Process. Technol. 2017, 159, 436-441.
[c]Reference catalyst, data retrieved from Catal. Sci. Technol. 2013, 3, 1324-1332.
[d]Reference catalyst, data retrieved from ACS Catal. 2017, 7, 5500-5512.

[a] Reaction conditions: 543 K, 5 MPa, and molar H$_2$/CO=2. HA=higher alcohols, MeOH=methanol, HC==alkenes, and HC—=alkanes. [b] Reference catalyst, data retrieved from *Fuel Process. Technol.* 2017, 159, 436-441. [c] Reference catalyst, data retrieved from *Catal. Sci. Technol.* 2013, 3, 1324-1332. [d] Reference catalyst, data retrieved from *ACS Catal.* 2017, 7, 5500-5512.

Reduced CNF-2-0.005 and K/CuFe/CNF-2-0.005 were additionally analysed by STEM-EDX. In the former (see FIG. 1c), the particles were mostly visualised inside the CNF channels. The average Cu and Fe particle sizes were calculated at 15.0 and 5.9 nm, respectively. Compared to the K-free CNF-2, the interaction between Cu and Fe was found to be superior, not only because of the better contact, as represented by the two particles detected at the pore mouth of a nanofibre, but also because less isolated Fe particles were observed. Based on fringe analysis of the corresponding HRTEM image, the Cu(111) and Fe(011) planes were identified.

When K was incorporated subsequently to Cu and Fe (FIG. 1b) large particles of Cu (17.8 nm) and Fe (8.8 nm) formed, which featured a poorer interaction, both in terms of contact area and the number of neighbouring aggregates.

To shed light onto the electronic effects of K, CNF-2-0.005 and K/CuFe/CNF-2-0.005 were characterised by H$_2$-TPD along with selected K-free samples, i.e., the counterpart of the former, CNF-2, and the poorly performing CR-CNF-2. H$_2$-TPD has been applied by several groups to investigate the H$_2$ adsorption ability of the metals and has always been performed under ambient conditions. In this example, the measurements have been conducted under the same pressure as it was applied in the tests. Specifically, the reduced catalysts were reactivated in a diluted H$_2$ flow at 573 K and 0.5 MPa for 3 h, as done in the catalytic reactor prior to the runs, exposed to 60 vol % of H$_2$ at 5 MPa and 543 K as upon reaction, flushed with He at the same pressure and temperature, and then heated in the inert stream up to 1103 K.

Testing of the promoted catalysts indicated that the simultaneous addition of small amounts of K to Cu and Fe during synthesis (CNF-2-0.005 and CNF-2-0.01) increased the selectivity towards HA, alkenes and CO$_2$, and reduced that state of the art CuFe catalyst (47%) over CNF-2-0.01. For the latter, the CO$_2$ selectivity raised to 18%, which is still much lower than for the reference material (28%). It was noteworthy that the selectivity to alkenes surpassed that of alkanes (15 vs. 14%). The addition of greater K amounts (CNF-2-0.1) led to the predominant production of CO$_2$ (60%) and the HA selectivity was lowered to 15%.

The alkali effect of minimising methanol formation was more pronounced at higher contents, though. The methanol selectivity decreased from 12 to 0.3%. Since stronger promotion also reduced the CO conversion, the highest STY of HA was obtained over CNF-2-0.005 (0.28 g$_{HA}$ g$_{cat}^{-1}$ h$^{-1}$). When K was introduced prior to the deposition of the active metals, the HA selectivity was similar to that of the K-free CNF-2 (30%) but more CO$_2$ was formed (18 vs. 6%) at the expense of paraffins and methanol. When the promoter was added after Cu and Fe, the HA selectivity reduced drastically to 9% and CO$_2$ was the most abundant product (37%). Fe/CuK/CNF-2-0.005 also exhibited a low selectivity towards HA but generated more alkanes (46%) and less CO$_2$ (21%).

STEM-EDX and HRTEM were conducted to assess the metals morphology, distribution and speciation in CNF-2-0.005 after the reaction. The mapping pointed to a higher fraction of particles located at the fibres' outer surface compared to the reduced solid. The particle size and interaction between Cu and Fe were preserved. A core-shell structure was detected in Fe-containing particles. Based on HRTEM, these comprised amorphous carbon in the outer layer and Fe$_2$C as the inner core. The (111) plane of this carbide was identified upon fringe analysis. Based on XPS, the surface Cu/Fe ratio was lowered from 1.6 to 1.3. This change is attributed to the moderately increased agglomeration of Fe (5.9 to 6.7 nm).

Overall, the catalytic and characterisation data for promoted systems corroborate the conclusions drawn for the K-free materials with respect to the fact that higher HA selectivity is obtained if the Cu particles are around 10 nm in size, Fe is not too dispersed, and a good interaction is established between the two active metals. The addition of K in small quantities enables the formation of a slightly more aggregated Fe phase, which has similar or even improved contact with Cu, minimising alkanes formation and boosting HA and olefins production. Thus, K plays an important structural role. In addition, electronic effects are also likely. $H_2$-TPD suggests an enhanced but more labile binding of $H_2$ to the metals, which shall help to slow the kinetics of hydrogenation reactions. This further substantiates the scarce relevance of the surface Cu/Fe ratio as a stand-alone descriptor.

Example 3: Acidic Material

MFI zeolites with nominal Si/Al molar ratios of 40 and 140 (CBV8014 for 40 and CBV28014 for 140, Zeolyst Ltd., denoted as MFI-x, where x is the Si/Al molar ratio) and FER zeolites with nominal Si/Al molar ratio of 27.5 (CP 914, Zeolyst Ltd., denoted as FER30) were delivered in ammonium form and calcined as described above, to convert them into the corresponding protonic forms. MFI-40 samples partially ($KMFI-40_p$) were obtained by treatments of the as-received MFI-40 in aqueous $KNO_3$ (1.0 mM and 0.1 M, respectively, 10 $g_{zeolite}$ $dm^{-3}$, 8 h). The zeolite recovered by filtration was washed with deionized water (1 $dm^3$ $g_{zeolite}^{-1}$), dried, and calcined under the same conditions as for the other samples.

USY zeolites with nominal Si/Al molar ratio of 40 (CBV780, Zeolyst Ltd., denoted as USY40), BEA zeolites with nominal Si/Al molar ratio of 90.5 (HCZB150, Clariant, denoted as BEA90), and MOR zeolites with nominal Si/Al molar ratio of 110 (690HOA, TOSOH, denoted as MOR110) were delivered in protonic form and used as received.

Table 3 summarizes the characterization data of the different acidic materials used in the present examples.

TABLE 3

Characterization data of the acidic materials with different acidity and porosity used as acidic materials.

| Acidic materials | $V_{pores}^a$ ($cm^3$ $g^{-1}$) | $S_{BET}^{b,d}$ ($m^2$ $g^{-1}$) | $C_{BAS}^c$ (μmol $g^{-1}$) | $C_{LAS}^c$ (μmol $g^{-1}$) |
|---|---|---|---|---|
| FER30 | 0.22 | 369 | 157 | 29 |
| MFI-40 | 0.25 | 399 | 176 | 23 |
| MFI-140 | 0.23 | 369 | 99 | 14 |
| $KMFI-40_p$ | 0.24 | 384 | 51 | 11 |
| USY40 | 0.52 | 734 | 52 | 8 |
| BEA90 | 0.50 | 555 | 60 | 8 |
| MOR110 | 0.30 | 465 | 47 | 30 |

$^a$Volume adsorbed at $p/p_0 = 0.99$; wherein $p/p_0$ is defined as the relative pressure of equilibrium gas pressure (p) to the saturation pressure ($p_0$).
$^b$BET method.
$^c$FTIR spectroscopy of adsorbed pyridine.
$^d$Mesoporous surface area determined by the t-plot method in bracket.

A combination of an acidic zeolite material with a CuFe catalyst deposited on carbon-containing support has been used in order to catalyze the conversion of the alkenes into higher alcohols. Before being deposited on a carbon-containing support, the iron precursor and the copper precursor have been coprecipitated with a promoter.

Example 4: Mixed-Bed Configured Reactor

A mixed-bed of a catalyst composition comprising KCuFe deposited on nanofibers as carbon-containing support and the acidic material MFI-40, obtained through physical mixing has been tested. The results have been compared with the use of the KCuFe deposited on nanofibers as carbon-containing support in the absence of the zeolite (see Table 4).

TABLE 4

Comparison between the performance data of the KCuFe/CNF used alone and the KCuFe/CNF and MFI-40 in a mixed-bed configured reactor. WHSV is expressed in $cm^3$ $g_{cat}^{-1}$ $h^{-1}$.
Reaction conditions: 543 K (269.85° C.), 5.0 MPa, molar ratio $H_2/CO = 2/1$.

| Catalyst | WHSV | $X_{CO}$ (%) | $S_{MeOH}$ (%) | $S_{DME}$ (%) | $S_{HA}$ (%) | $S_{1-HA}$ (%) | $S_{2-HA}$ (%) | $S_{alkenes}$ (%) | $S_{alkanes}$ (%) | $S_{CO2}$ (%) |
|---|---|---|---|---|---|---|---|---|---|---|
| KCuFe/CNF | 34000 | 4 | 10 | 0 | 38 | 35 | 3 | 20 | 19 | 13 |
| KCuFe/CNF$^\#$ | 32000 | 11 | 7 | 0 | 37 | 35 | 2 | 19 | 27 | 10 |
| KCuFe/CNF + MFI-40 | 8000 | 10 | 0 | 6 | 33 | 11 | 22 | 5 | 42 | 14 |
| KCuFe/CNF + MFI-40 | 20000 | 4 | 0 | 3 | 35 | 21 | 14 | 8 | 39 | 15 |

$^\#$Reaction conditions: 548 K (274.85° C.), 5.0 MPa, molar ratio $H_2/CO = 1.5/1$.

The results, when the process is carried out using a catalyst composition mixed with the MFI acidic material, shows that a selectivity into C2+ alcohols of at least 30% can be achieved, which his slightly lower than the selectivity in the absence of zeolite. However, these results show that the generation of 2-HA has been favoured. A considerable fraction of 1-HA has been thus transformed into alkanes and carbon dioxide. Advantageously, no methanol at all was generated and the generation of undesirable carbon dioxide has been contained in the same proportion (i.e. 10-15%) as it was generated with the catalyst used in the absence of MFI zeolite.

In order to achieve a better selectivity in the generation of C2+ alcohols than when the catalyst alone was used, it has been decided to combine the zeolite in a separate bed, which is placed downstream of the reactive bed containing the catalyst alone.

Example 5: Dual-Bed Configured Reactor and MFI Zeolites as Acidic Material

A first reactive bed loaded with a catalyst composition comprising KCuFe deposited on nanofibers as carbon-containing support and a second reactive bed loaded with an acidic material based on MFI zeolites have been prepared within one reactor. The results have been compared with the use of the KCuFe deposited on nanofibers as carbon-containing support in the absence of the zeolite (see Table 5).

TABLE 5

Comparison between the performance data of the KCuFe/CNF used alone and the KCuFe/CNF with MFI zeolites in a dual-bed configured reactor. WHSV is expressed in cm³ $g_{cat}^{-1}$ h$^{-1}$. Reaction conditions: 543 K (269.85° C.), 5.0 MPa, molar ratio $H_2$/CO = 2/1, CO conversion rate of 4%.

| Catalyst | WHSV | $X_{CO}$ (%) | $S_{MeOH}$ (%) | $S_{DME}$ (%) | $S_{HA}$ (%) | $S_{1-HA}$ (%) | $S_{2-HA}$ (%) | $S_{alkenes}$ (%) | $S_{alkanes}$ (%) | $S_{CO2}$ (%) |
|---|---|---|---|---|---|---|---|---|---|---|
| KCuFe/CNF | 34000 | 4 | 10 | 0 | 38 | 35 | 3 | 20 | 19 | 13 |
| KCuFe/CNF + MFI-40 | 32000 | 4 | 0 | 7 | 42 | 18 | 24 | 8 | 29 | 14 |
| KCuFe/CNF + MFI-140 | 32000 | 4 | 0 | 3 | 44 | 36 | 8 | 12 | 24 | 17 |
| KCuFe/CNF + KMFI-40$_p$ | 32000 | 4 | 1 | 5 | 47 | 38 | 9 | 12 | 27 | 8 |
| KCuFe/CNF + KMFI-40$_p$ | 32000# | 8 | 0 | 6 | 45 | 32 | 13 | 11 | 25 | 13 |

Reaction conditions: 573 K (299.85° C.), 5.0 MPa, molar ratio $H_2$/CO = 1.0/1, CO conversion rate of 8%.

Using a reactor configured with two reactive beds arranged in series for performing a syngas conversion, the selectivity of C2+ alcohols has been drastically increased. The selectivity of C2+ alcohols is indeed above 40% at a CO conversion rate of 4%. The small amount of methanol (1%) that is sometimes generated can be controlled by adapting the reaction conditions. It is also highlighted that by comparison with the results obtained when a mixed bed is used, the selectivity can be shifted again toward to formation of primary alcohols (1-HA), which help to reduce the generation of alkanes and carbon dioxide.

When the less acidic material, namely MFI-140, is used, the selectivity into C2+ alcohols has reached 44% but 1-HA conversion to alkanes and $CO_2$, as well as alkenes hydration to 2-HA were better balanced.

In order to further reduce the acidity of the second bed, MFI-40 was partially exchanged with K to produce KMFI-40$_p$, which possessed half as many $C_{BAS}$ compared to MFI-140 (51 μmol g$^{-1}$ for KMFI-40$_p$ versus 99 μmol g$^{-1}$ for MFI-140, see Table 3). This approach was advantageous since the HA selectivity further slightly increased reaching 47% and the $CO_2$ selectivity dropped to 8%.

By tuning of the reaction parameters (573 K, 5 MPa, $H_2$/CO=1, and WHSV=32000 cm³ $g_{cat}^{-1}$ h$^{-1}$), an HA selectivity of 45% was attained at a doubled CO conversion rate (8%). Under these conditions, the $STY_{HA}$ was 0.61 $g_{HA}g_{cat}^{-1}$ h$^{-1}$, which was 15% higher than obtained over the KCuFe/CNF system alone (0.53 $g_{HA}g_{cat}^{-1}$ h$^{-1}$). Moreover, taking into account the restricted production of side-products, such as MeOH, $CO_2$ and DME, and the space-time yield of this reaction which is similar to those reported with a catalyst deposited on multiwalled carbon nanotubes, based on Co—Cu (0.611 $g_{HA} g_{cat}^{-1}$ h$^{-1}$) or on Co—Mo—K oxide (0.628 $g_{HA} g_{cat}^{-1}$ h$^{-1}$) in the absence of an acidic material, the implementation of an acidic material in combination with a catalyst composition based on copper and iron (which is more available and affordable than cobalt) is very useful.

Example 6: Dual-Bed Configured Reactor and Miscellaneous Zeolites as Acidic Material To explore the role of the zeolite framework, BEA90, MOR110, and USY40 were alternatively applied. These are zeolites that possess similar acidity to KMFI-40$_p$ ($C_{BAS}$<60 μmol g$^{-1}$). The results have been compared with the use of the KCuFe deposited on nanofibers as carbon-containing support without the zeolite (see Table 6).

TABLE 6

Comparison between the performance data of the KCuFe/CNF used alone with the KCuFe/CNF and miscellaneous_zeolites in a dual-bed configured reactor. WHSV is expressed in cm³ $g_{cat}^{-1}$ h$^{-1}$. Reaction conditions: 543 K (269.85° C.), 5.0 MPa, molar ratio $H_2$/CO = 2/1, CO conversion rate of 4%.

| Catalyst | WHSV | $X_{CO}$ (%) | $S_{MeOH}$ (%) | $S_{DME}$ (%) | $S_{HA}$ (%) | $S_{1-HA}$ (%) | $S_{2-HA}$ (%) | $S_{alkenes}$ (%) | $S_{alkane}$ (%) | $S_{CO2}$ (%) |
|---|---|---|---|---|---|---|---|---|---|---|
| KCuFe/CNF | 34000 | 4 | 10 | 0 | 38 | 35 | 3 | 20 | 19 | 13 |
| KCuFe/CNF + MFI-40 | 32000 | 4 | 0 | 7 | 42 | 18 | 24 | 8 | 29 | 14 |
| KCuFe/CNF + KMFI-40$_p$ | 32000 | 4 | 1 | 5 | 47 | 38 | 9 | 12 | 27 | 8 |
| KCuFe/CNF + FER30 | 32000 | 4 | 3 | 1 | 35 | 31 | 4 | 13 | 31 | 18 |
| KCuFe/CNF + USY40 | 32000 | 4 | 4 | 1 | 44 | 34 | 10 | 11 | 24 | 16 |
| KCuFe/CN + BEA90 | 32000 | 4 | 3 | 1 | 48 | 42 | 6 | 11 | 23 | 14 |
| KCuFe/CN + MOR110 | 32000 | 4 | 1 | 1 | 50 | 45 | 5 | 13 | 25 | 10 |
| KCuFe/CN + MOR110 | 32000# | 8 | 1 | 0 | 52 | 47 | 5 | 13 | 22 | 13 |

Reaction conditions: 573 K (299.85° C.), 5.0 MPa, molar ratio $H_2$/CO = 1.0/1, CO conversion rate of 8%.

In the presence of BEA90 and MOR110, the HA selectivity was slightly higher than obtained using KMFI-40$_p$ due to the formation of additional 1-HA rather than 2-HA. Methanol was retained to a greater extent (3% or less) and almost no DME was generated (1% or less).

The alkanes selectivity was moderately lower, and the alkenes and $CO_2$ selectivities were slightly more pronounced.

KCuFe/CNF+USY40 exhibited an inferior HA selectivity mainly due to a suppression of 1-HA and a higher $CO_2$ selectivity.

Ferrierite (FER30) with an acidity similar to MFI-40 ($C_{BAS}$ of 157 μmol g$^{-1}$ for FER30 and $C_{BAS}$ of 176 μmol g$^{-1}$ for MFI-40, see Table 3) was additionally investigated. While its application is not appealing from a practical perspective, it is interesting to note that the selectivity patterns strongly deviates from that determined using MFI-40 suggesting a strong role of the pore topology. In spite of a high 1-HA selectivity over KCuFe/CNF+FER30 compared to KCuFe/CNF+MFI-40 (31% versus 18%), the 2-HA selectivity was very low (4% versus 24%).

Figure 3:
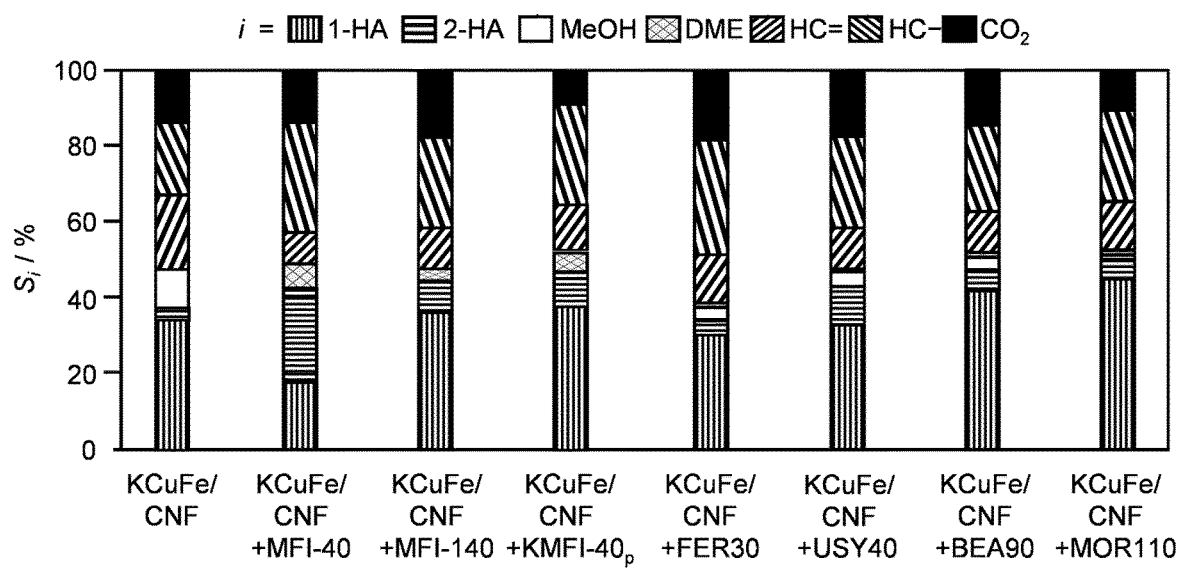
FIG. 3 shows the selectivity to different products at a CO conversion rate of 4% over hybrid beds comprising a K-promoted CuFe catalyst deposited on carbon nanofibers and zeolites with different framework and acidity.

FIG. 3 shows the selectivities to the different products obtained at reaction conditions of 543 K (269.85° C.), 5.0 MPa with a molar ratio $H_2/CO=2/1$, at CO conversion rate of 4%, in a dual-bed configured reactor. Overall, KMFI-40$_p$, BEA90 and MOR110 stand as the most attractive zeolites since they enhance HA formation (selectivity into HA superior to 45%) while keeping the MeOH, $CO_2$ and DME selectivities at a low level (less than 3%, less than 15% and less than 5%, respectively).

Example 7: CO Conversion Rate of 8%

When testing the hybrid beds containing these materials at 573 K (299.85° C.) instead of 543 K (269.85° C.) and a molar $H_2/CO$ ratio of 1 rather than 2, a doubled CO conversion rate (8%) was attained in both cases and the HA selectivity reached respectively 45% and 52% for KCuFe/CNF+MFI-40$_p$ and KCuFe/CNF+MOR110 (see Table 7).

TABLE 7

Comparison between the performance data of the best system of the present disclosure and data from the prior art.

| Catalyst | $X_{CO}$ (%) | $S_{MeOH}$ (%) | $S_{DME}$ (%) | $S_{HA}$ (%) | $S_{alkane}$ (%) | $S_{CO2}$ (%) | $STY_{HA}$ ($g_{HA}g_{cat}^{-1}$ $h^{-1}$) |
|---|---|---|---|---|---|---|---|
| KCuFe/CNF + KMFI-40$_p$# | 8 | 0 | 6 | 45 | 25 | 13 | 0.61 |
| KCuFe/CNF + MOR110# | 8 | 1 | 0 | 52 | 22 | 13 | 0.70 |
| Co$_3$Cu/CNT## | 38.5 | — | 11.4 | 57.9 | 20.7 | 5.0 | 0.611 |
| CoMoK$_{0.05}$/CNT### | 21.1 | 10.5 | — | 76.2 | 22.1 | 22.5 | 0.628 |

Reaction conditions: 573 K (299.85° C.), 5.0 MPa, WHSV = 32000 cm$^3$ $g_{cat}^{-1}$ h$^{-1}$, molar ratio $H_2/CO$ = 1.0/1.
X. Dong et al., Catalysis Today, 147 (2009), 158-165.
(Reaction conditions: 5.0 MPa, 573 K (299.85° C.), GHSV = 7200 cm$^3$ $g_{cat}^{-1}$ h$^{-1}$, molar ratio $H_2/CO$ = 1.0/1).
X-M. Wu et al., Applied Catalysis A, 340 (2008) 87-97
(Reaction conditions: 5.0 MPa, 593 K (319.85° C.), GHSV = 10000 cm$^3$ $g_{cat}^{-1}$ h$^{-1}$, molar ratio $H_2/CO$ = 2.0/1).

Using MOR110 as acidic material, the $STY_{HA}$ Was 0.70 $g_{HA}g_{cat}^{-1}$ h$^{-1}$, which was 32% higher than obtained over the KCuFe/CNF system alone (0.53 $g_{HA}g_{cat}^{-1}$ h$^{-1}$). This productivity is superior to that of the best HAS catalysts reported (at most 0.63 $g_{HA}g_{cat}^{-1}$ h$^{-1}$). The higher $STY_{HA}$ is due to the application of the higher WHSV and lower $H_2/CO$ ratio than in the examples of the prior art

The invention claimed is:

1. Process for converting syngas to C2+ alcohols said process comprising the following steps:
   a) providing an installation comprising at least one reactor having one or more catalytic beds;
   b) providing a catalyst composition and one or more acidic materials within said at least one reactor;
   c) providing a feed stream comprising a mixture of $H_2$ and CO;
   d) contacting said feed stream with said catalyst composition and said one or more acidic materials under reaction conditions to provide product stream;
   characterized in that
   said catalyst composition comprises an active phase comprising CuFe deposited on a carbon-containing support, the total content of iron and copper ranging from 1 to 10 wt. % based on the total weight of the catalyst composition and as determined by inductively coupled plasma optical emission spectroscopy, and the one or more acidic materials being one or more zeolites having a Si/Al molar ratio ranging between 2 and 200 as determined by inductively coupled plasma-optical emission spectroscopy.

2. The process according to claim 1, wherein said at least one reactor comprises a first reactive bed and one or more subsequent reactive beds, one or more subsequent reactive beds being arranged downstream of the first reactive bed, the process is characterized in that the catalyst composition and the one or more acidic materials are provided in different reactive beds, and in that the catalyst composition is provided in the first reactive bed and the one or more acidic materials are provided in the one or more subsequent reactive beds.

3. The process according to claim 1, wherein said at least one reactor comprises a first reactive bed and one or more optional subsequent reactive beds, wherein the one or more subsequent reactive beds, when present, are arranged downstream of the first reactive bed, the process is characterized in that during step (b) a mixture of the catalyst composition and of the one or more acidic materials is provided in the first reactive bed.

4. The process according to claim 1, characterized in that the carbon-containing support of the catalyst composition is selected from carbon nanofibers and/or carbon nanotubes.

5. The process according to claim 4, characterized in that said carbon-containing support has a hollow-core structure with an inner diameter of at least 17 nm as determined according to $N_2$ sorption analysis; and/or, in that the carbon-containing support is or comprises carbon nanofibers selected from platelet-type carbon nanofibers and conical platelet-type carbon nanofibers.

6. The process according to claim 1, characterized in that the catalyst composition further comprises at least one promoter.

7. The process according to claim 1, characterized in that the catalyst composition has a Cu/Fe bulk molar ratio is ranging from 0.5/1 to 5/1; and/or in that the catalyst composition is reduced over hydrogen gas before step (c).

8. The process according to claim 1, characterized in that the Cu particle size in the catalyst composition is at least 7 nm as determined from the (111) reflection in an XRD pattern using the Scherrer equation; or the Cu particle size in the catalyst composition is at most 35 nm as determined from the (111) reflection in a XRD pattern using the Scherrer equation.

9. The process according to claim 1, characterized in that the one or more acidic materials are one or more zeolites are selected from MFI, FAU, MOR, FER, BEA, TON, MTT, or OFF families.

10. The process according to claim 1, characterized in that the one or more acidic materials are one or more zeolites partially ion-exchanged with an alkali metal-based ion.

11. The process according to claim 1, characterized in that the one or more acidic materials are one or more zeolites having a surface area comprised between 10 m$^2$ g$^{-1}$ and 1000 m$^2$ g$^{-1}$, as determined by the Brunauer-Emmett-Teller (BET) method; and/or in that the one or more acidic materials are one or more zeolites having a pore volume comprised between 0.15 cm$^3$ g$^{-1}$ and 1.25 cm$^3$ g$^{-1}$, as determined by N$_2$ sorption analysis.

12. The process according to claim 1, characterized in that the one or more acidic materials are one or more zeolites having a density of Brønsted-acid sites ranging from 5 µmol g$^{-1}$ to 700 µmol g$^{-1}$ as determined by Fourier transform infrared spectroscopy of adsorbed pyridine; and/or in that the one or more acidic materials are one or more zeolites having a density of Lewis-acid sites ranging from 4 µmol g$^{-1}$ to 250 µmol g$^{-1}$ as determined by Fourier transform infrared spectroscopy of adsorbed pyridine.

13. The process according to claim 2, wherein said at least one reactor comprises a first reactive bed, the process is characterized in that the reaction conditions in the first reactive bed comprise:

a reaction temperature ranging from 443 K (169.85° C.) to 653 K (379.85° C.), and/or a reaction pressure range ranging from 1 MPa to 10 MPa, and/or a weight hourly space velocity ranging from 500 cm$^3$ g$_{cat}^{-1}$ h$^{-1}$ to 48,000 cm$^3$ g$_{cat}^{-1}$ h$^{-1}$.

14. The process according to claim 2, wherein said at least one reactor comprises one or more subsequent reactive beds being arranged downstream of the first reactive bed, the process is characterized in that the reaction conditions in the one or more subsequent reactive beds comprise one or more of:

a reaction temperature ranging from 373 K (99.85° C.) to 773 K (499.85° C.), and/or a reaction pressure range ranging from 0.1 MPa to 10.0 MPa; and/or a weight hourly space velocity ranging from 500 cm$^3$ g$_{cat}^{-1}$ h$^{-1}$ to 50,000 cm$^3$ g$_{cat}^{-1}$ h$^{-1}$.

* * * * *